United States Patent [19]
Weichselbaum et al.

[11] Patent Number: 5,641,755
[45] Date of Patent: Jun. 24, 1997

[54] REGULATION OF X-RAY MEDIATED GENE EXPRESSION

[75] Inventors: Ralph R. Weichselbaum, Chicago; Dennis E. Hallahan, Park Ridge, both of Ill.; Donald W. Kufe, Wellesley, Mass.

[73] Assignees: Arch Development Corp., Chicago, Ill.; Dana-Farber Cancer Institute, Boston, Mass.

[21] Appl. No.: 278,452

[22] Filed: Jul. 20, 1994

Related U.S. Application Data

[63] Continuation-in-part of Ser. No. 192,107, Feb. 4, 1994, abandoned.
[51] Int. Cl.$^6$ .................................................. A61K 48/00
[52] U.S. Cl. .......................... 514/44; 424/9.2; 435/6; 435/29; 514/396; 935/36; 935/62; 536/24.1
[58] Field of Search .................. 424/9.1, 1.11; 514/44, 396; 435/172.1, 172.3, 240.2, 6, 29; 536/24.1; 935/36, 62

[56] References Cited

PUBLICATIONS

Arai et al (1990) Ann Rev Biochem 59: 783–784.
Culver et al (1994) Trends in Genetics 10:174–178.
Miller et al (1995) FASEB J 9:190–199.
Hodgson (1995) Exp Opin Ther Patents 5: 459–468.
Marshall (1995) Science 269: 1050–1055.
Weichselbaum et al (1992) Int J Radiation Oncology Biol Phys 24: 565–567.
Van Zee et al (1992) Proc Natl Acad Sci USA 89: 4845–4849.
MacIntyre et al (1991) Int J Immunopharmac 13: 175–184.
Brach et al (1991) J Clin Invest 88: 691–695.
Hallahan et al (1991) Cancer Research 51: 4565–4569.
Sherman et al., "Ionizing raddiation regulates expression of the c–jun proto–oncogene," *Proc. Am. Assoc. Cancer Res.*, 31(0) :13, 1990.

Hallahan et al., "Transcriptional regulation of the TNF gene by x–irradiation," *Proc. Am. Assoc. Cancer Res.*, 31(0) :75, 1990.

Baumann et al., "Response of Xenografts of Human Malignant Gliomas and Squamous Cell Carcinomas to Fractionated Irradiation," *J. Radiation Oncology Biol. Phys.*, 23(4) :803–809, 1992.

Budach et al., "The TCD$_{50}$ and Regrowth Delay Assay in Human Tumor Xenografts: Differences and Implications," *Int. J. Radiation Oncology Biol. Phys.*, 25(2) :259–268, 1993.

Gustafson et al., "Hydrogen Peroxide Stimulates Phospholipase A$_2$—Mediated Archidonic Acid Release in Cultured Intestinal Epithelial Cells (INT 407)," *Archidonic Acid Release*, 26:237–247, 1991.

Hallahan et al., "Inhibition of Protein Kinases Sensitizes Human Tumor Cells to Ionizing Radiation," *Radiation Research*, 129:345–350, 1992.

(List continued on next page.)

*Primary Examiner*—Bruce R. Campell
*Attorney, Agent, or Firm*—Arnold, White & Durkee

[57] ABSTRACT

Treatment of cells with ionizing radiation is associated with the production of arachidonic acid. Inhibition of phospholipase A2 abolishes radiation-mediated arachidonate production, protein kinase C induction and tumor necrosis factor gene expression. The addition of inhibitors of lipoxygenase, such as ketoconazole, prior to irradiation reduces the expression of of tumor necrosis factor while maintaining the expression of other radiation inducible genes, such as Egr-1 and c-jun. In contrast, indomethacin, an inhibitor of cyclooxygenase, enhanced the expression of tumor necrosis factor as well as other radiation inducible genes. The results show that lipoxygenase inhibitors are useful in the treatment of radiation-induced mucositis, dermatitis, pneumonitis, proctitis, and esophagitis. which may be due to the production of cytokines such as TNF.

4 Claims, 5 Drawing Sheets

OTHER PUBLICATIONS

Kastan et al., "A Mammalian Cell Cycle Checkpoint Pathway Utilizing p53 and GADD45 Is Defective in Ataxia-Telangiectasia," *Cell*, 71:587–597, 1992.

Nishizuka, "Intracellular Signaling by Hydrolysis of Phospholipids and Activation of Protein Kinase C," *Science*, 258; 607–614, 1992.

Peppelenbosch et al., "Epidermal Growth Factor-Induced Actin Remodeling Is Regulated by 5–Lipoxygenase and Cyclooxygenase Products," *Cell* 74:565–575, 1993.

Rao et al., "Hydrogen Peroxide–induced c–fos Expression is Mediated by Arachidonic Acid Release: Role of Protein Kinase C," *Nucleic Acids Research*, 21(5) :1259–1263, 1993.

Sherman et al., "Regulation of Tumor Necrosis Factor Gene Expression by Ionizing Radiation in Human Myeloid Leukemia Cells and Peripheral Blood Monocytes," *J. Clin. Invest.*, 87:1794–1797.

Spriggs et al., "Phospholipase $A_2$ Activation and Autoinduction of Tumor Necrosis Factor Gene Expression by Tumor Necrosis Faction," *Cancer Research*, 50:7101–7107, 1990.

Ward et al., "The Pulmonary Response to Sublethal Thoracic Irradiation in the Rat," *Rad. Res.*, 136:15–21, 1993.

Ward et al., "The Effect of Steroids on Radiation–Induced Lung Disease in the Rat," *Rad. Res.*, 136:22–28, 1993.

Yates et al., "A New Non Redox 5–Lipoxygenase Inhibitor ICI D2138 is Well Toolerated and Inhibits Blood Leukotriene Synthesis in Healthy Volunteers," *American Review of Respiratory Disease*, 145(4) :A745, 1992.

Zhou and Elledge, "Isolation of crt Mutants Constitutive for Transcription of the DNA Damage Inducible Gene RNR3 in *Saccharomyces cerevisiae*," *Genetics* 131:851–866, 1992.

REGULATION OF X-RAY MEDIATED GENE EXPRESSION

The present application is a continuation-in-part of U.S. patent application Ser. No. 08/192,107, filed Feb. 4, 1994 now abandoned. The entire text of the above-referenced disclosures is specifically incorporated by reference herein without disclaimer.

The government owns rights, in the present invention pursuant to NIH grant numbers CA58508, CA41068, and CA42586.

BACKGROUND OF THE INVENTION

1. Field of the Invention

The present invention relates generally to the fields of radiation biology and cell biology. More particularly, it concerns the attenuation of the effect of ionizing radiation induced activation of cytokines, such as tumor necrosis factor, by inhibitors of extranuclear signal transduction.

2. Description of the Related Art

Tumor necrosis factor (TNF) is a polypeptide mediator of the inflammatory response and induces proliferation of fibroblasts, recruitment of inflammatory cells, activation of endothelial cells and hemorrhagic necrosis of tumors in mice (Fiers, 1991). Tumor necrosis factor also kills tumor cells directly through the induction of free radical formation and DNA fragmentation. These effects may explain the mechanism by which TNF enhances tumor cell killing by x-rays (Hallahan et al., 1990, Hallahan et al., 1989). Increased production of TNF is associated with inflammatory disorders such as autoimmune demyelination of the central nervous system and respiratory distress syndrome (Fiers, 1991).

Tumor necrosis factor is produced by monocytes and macrophages in response to diverse stimuli, including ionizing radiation (Sherman et al., 1991, Wasserman et al., 1991). Increased TNF serum levels are associated with acute and subacute sequelae following total body irradiation (Holler et al., 1990). Radiation sequelae that correlate with TNF serum levels include pneumonitis, endothelial leakage syndrome, and veno-occlusive disease. Although, the effects of ionizing radiation on rapidly proliferating cell renewal systems have classically been theorized to be due to direct killing of stem cells within the injured organ, other work has suggested that TNF induction plays a role in the acute effects of irradiation by directly enhancing cell killing as well as mimicking the acute inflammatory response (Wong et al., 1991).

Signaling pathways activated by DNA damage contribute to survival of prokaryotes and eukaryotic cells following exposure to x-rays or UV light. In irradiated *E. coli*, damaged DNA forms a complex with the Rec A protease resulting in the transcriptional induction of a variety of genes including those encoding DNA repair enzymes (Walker, 1985). In yeast, UV light and x-rays result in the induction of genes which participate in the repair of damaged DNA (Jones et al., 1991, Cole et al., 1987). Genes whose products are proposed to recognize damaged or un-replicated DNA and to participate in intracellular signaling that regulates cell cycle progression and DNA repair have been identified in *S. cerevisiae* and *S. pombe* (House et al., 1992, Enoch et al., 1992). The complexity of this signaling pathway is demonstrated by the number of genes involved in sensing DNA damage and transmitting the signal (Enoch et al., 1992). DNA damage is presumed to be the initiating event in mammalian cell induction of stress response genes following x-ray or UV exposure (Herrlich et al., 1992, Kastan et al., 1992). However, the mechanisms of DNA damage recognition have not been identified in mammalian cells.

Signal transduction pathways activated by ionizing radiation include increased phosphotransferase activity of cytoplasmic protein kinases (Hallahan et al., 1991a, Hallahan et al., 1991b, Uckun et al., 1992). Moreover, inhibition of protein kinases blocks radiation-mediated gene induction and effects diverse biological endpoints such as apoptosis (Uckun et al., 1992), radiation survival (Hallahan et al., 1992)) and induction of the cytokine tumor necrosis factor (TNF) (Hallahan et al., 1991b). The calcium/phospholipid-dependent protein kinase (PKC) is activated within 15 seconds of ionizing radiation exposure and is extinguished by 90 seconds in human leukemia HL-60 cells (Hallahan et al., 1991b).

Second messengers that participate in PKC activation following exposure to external stimuli include free fatty acids such as arachidonic acid (Nishizuka, 1992). Previous studies have suggested that phospholipase A2-mediated hydrolysis of oxidized membrane phospholipids is a primary means of bioreduction following oxidative injury (Au et al., 1983, Sevanian et al., 1983)(reviewed in van Kuijk et al., 1987). For example, arachidonic acid release is increased following treatment with $H_2O_2$ due to hydrolysis of oxidized membrane phospholipids (Gustafson et al., 1991, Shasby et al., 1988). To determine whether arachidonic acid production was associated with radiation-mediated signal transduction, arachidonic acid production was quantified in irradiated HL-60 cells and found an increase in arachidonate within 30 minutes following irradiation.

Since phospholipase A2 hydrolysis phosphatidylcholine to arachidonic acid, the effects of the phospholipase A2 inhibitors mepacrine (Rao et al., 1993), and bromphenylbromide (BPB) (Peppelenbosch et al., 1993) were investigated. In addition, the effects of dexamethasone and pentoxifylline on radiation-induced fatty acid hydrolysis were studied, as these agents have been shown to inhibit phospholipase A2, reduce the production of cellular mediators of inflammation and tissue injury, and inhibit lipopolysaccharide-induced TNF production in monocytes (Strieter et al., 1988, Hah et al., 1990). Moreover, glucocorticoids and pentoxifylline are employed clinically to prevent some acute toxicities of radiotherapy (Bianco et al., 1991, Phillips et al., 1975). The inventors determined that each agent attenuated arachidonic acid release into the medium of cells treated with X-rays or $H_2O_2$. Thus, extranuclear second messengers are in part responsible for radiation-mediated signal transduction and inhibition of this pathway may provide a means of attenuating the inflammatory-like response observed in irradiated tissues through the inhibition of TNF gene induction.

Radiation-mediated TNF induction is attenuated by inhibitors of phospholipase A2 and protein kinase C (PKC) Hallahan et al., 1994 (in press), Hallahan et al., 1991b). Phospholipase A2 hydrolyzes the membrane fatty acid phosphatidylcholine to form arachidonic acid and eliminates oxidized membrane lipid following exposure to oxidizing agents (Sevanian et al., 1991, van Kuijk et al., 1987). Inhibitors of this enzyme attenuate arachidonate production and PKC activation following treatment with X rays or $H_2O_2$ (8). Arachidonic acid is subsequently metabolized by lipoxygenase or cyclooxygenase to form leukotrienes or prostaglandins respectively. Moreover, arachidonic acid has been shown to activate PKC (Fan et al., 1990). Protein kinase C is rapidly and transiently activated following irradiation and mediates radiation-induction of certain genes, including TNF, Egr-1 and c-jun (Hallahan et al., 1991a, Hallahan et al., 1991b). Egr-1 and c-jun encode transcription factors and are associated with G1/S transition following mitogenic stimulation (Sukhatme et al. 1990). Since these radiation inducible genes are known to be induced through activation of both PKC-dependent and -independent pathways, the inventors investigated whether these signal transduction pathways are specific for radiation-mediated TNF induction.

Phospholipase A2 inhibitors used in clinical radiotherapy to ameliorate acute and subacute sequelae include glucocorticoids and pentoxifylline (Bianco et al., 1991, Phillips et al., 1975). Glucocorticoids are used to treat radiation induced proctitis, pneumonitis, conjunctivitis, external otitis, CNS syndromes and occasionally mucositis. Pentoxifylline is effective in preventing pneumonitis and mucositis following total body irradiation prior to bone marrow transplantation (Bianco et al., 1991). Taken together, these findings implicate phospholipase A2 in radiation-induced TNF induction and the acute sequelae of radiotherapy. Because arachidonic acid is metabolized by lipoxygenase and cyclooxygenase, inhibitors of these enzymes were added to cells prior to irradiation to determine whether signaling through these pathways contribute to radiation-induction of TNF and related molecules.

A surprising and unexpected advantage of the instant invention is the ability to selectively inhibit the expression of TNF or genes coupled to the TNF promoter, while simultaneously allowing expression of genes operatively linked to, for example, other radiation inducible promoters such as Egr and jun. This allows the selective induction of genes linked to radiation inducible promoters without the corresponding increase in tumor necrosis factor that may be involved in clinical symptoms of acute and subacute radiation induced sequelae.

SUMMARY OF THE INVENTION

The present invention, in a general and overall sense, concerns methods of inhibiting the production of cytokines, for example TNF, following exposure of cells to ionizing radiation. In accordance with these methods, cells are treated with inhibitors of lipoxygenase prior to exposure to ionizing radiation. In a preferred embodiment, preparations of ketoconazole are administered to cells prior to ionizing radiation exposure.

Although the invention has been illustrated with ketoconazole, other lipoxygenase inhibitors could be employed. Examples include but are not limited to fluconazole, itraconazole, AA 861, cirsiliol, zileuton, BWA4C, ICID2138, piriprost, or diethylcarbamazine.

In certain embodiments of the invention, methods are provided for the treatment of acute radiation sequelae that mimic local inflammatory reactions, such as pneumonitis, proctitis, mucositis, dermatitis, and esophagitis. These consequences of radiotherapy may be associated with cytokines, such as tumor necrosis factor, or with arachidonic acid metabolites.

A further embodiment of the invention is the amelioration of severe mucositis in immunocompromised patients who must undergo radiation therapy. Thus, lipoxygenase inhibitors may improve the therapeutic ratio in HIV patients receiving radiotherapy to, for example, the oropharyngeal mucosa.

A surprising and unexpected advantage of using lipoxygenase inhibitors is that the radiation-mediated tumor necrosis factor induction was abolished in cells pretreated with lipoxygenase inhibitors, however, the responsiveness of other radiation-inducible promoters, such as Egr-1, and c-jun, remained unchanged. This suggests that the lipoxygenase pathway participates in the overall signalling pathway leading to the induction of tumor necrosis factor, and further indicates that signal transduction through the lipoxygenase pathway is not a generalized pathway common to all radiation inducible promoters.

It is further contemplated that the methods of the instant invention will be applicable to related enzymes oxidizing arachidonic acid, for example, arachidonate 5-lipoxygenase and arachidonate 12-lipoxygenase.

The inhibition of tumor necrosis factor expression, while leaving unaffected the expression of other radiation inducible genes, is an important advantage in designing radiotherapy protocols. For example, protocols may be designed wherein it is desirable to prevent the formation of tumor necrosis factor due to its effects on radiation-induced sequelae, while at the same time inducing other radiation-inducible promoters that have been operatively linked to genes for desirable therapeutic proteins.

The invention contemplates methods using a variety of lipoxygenase inhibitors, including non-redox inhibitors or iron ligand inhibitors. Exemplary examples of non-redox inhibitors include ketoconazole, NDGA, fluconazole, itraconazole, AA 861, cirsiliol, zileuton, BWA4C, ICID2138, piriprost, or diethylcarbamazine.

Exemplary iron ligand inhibitors include zileuton, an orally effective inhibitor of 5-lipoxygenase that effectively inhibits leukotriene-dependent inflammation in mice and inflammatory cell influx in rats (McMillan et al., 1992). Doses employed include 800 mg, which inhibits leukotriene synthesis for approximately 6 hours. At 800 mg twice daily, significant relief of rheumatoid arthritis symptoms was demonstrated. A total daily dose of 3.2 g (800 mg four times daily) will provide sustained lipoxygenase inhibition. (McMillan et al. 1992). Other iron ligand inhibitors, such as BWA4C, are well absorbed and well tolerated and, at doses of 400 mg three times daily, produces a prolonged lipoxygenase inhibition that is maintained throughout a 24 hour period.

Non redox inhibitors that are envisioned to be useful in the scope of this invention include ICID2138, which produces potent, prolonged inhibition of 5-lipoxygenase in human volunteers (Yates, R. A. et al. 1992). Pharmacokinetic evaluation indicates that the half-life of ICID2318 is approximately 12 hours, indicating that one may employ once daily dosages for lipoxygenase inhibition.

The invention also contemplates an in vitro method of assessing growth inhibition in cells following radiation treatment, but without the interfering effects of cytokines, particularly TNF, that are induced after radiation exposure. For example, the radiation inducible promoters Egr and jun are largely unaffected by treatment with lipoxygenase inhibitors, while TNF induction is largely abolished in these same cells. Thus, the invention provides a ready method for evaluating the effects of proteins resulting from expressed genes operatively linked to Egr and jun and following radiation exposure, yet interference from cytokines such as TNF is largely abolished. A particular advantage of this method is that by eliminating TNF as a factor involved in cell survival, a skilled artisan may make choices relating to the selection of radiosensitizing or radioprotective agents to use in treatment protocols.

Studying the effects of such protocols on tumor cells in vitro is an effective means by which to assess the effectiveness of these new treatment methods. Model systems to assess the killing of transformed (cancerous) cells are known to be predictive of success in human treatment regimens, partly as the cell types are essentially the same and all malignant cells simply proliferate, having little interaction with other systems. This is different from the problems found using other more interactive biological systems, such as, for example, when studying components of the immune system in isolation.

However, other models designed to allow optimization of these methods will naturally be employed prior to translating to a clinical environment. In particular, one may assess the effects in various animal model systems of cancer, including those in which human cancer cells are localized within an animal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

The present invention relates generally to the preparation and use of lipoxygenase inhibitors to modulate the expression of radiation inducible promoters. More specifically, the lipoxygenase inhibitors of the present invention block x-ray induction of certain cytokines, such as tumor necrosis factor (TNF). A practical application of blocking cytokine production following x-ray exposure is to ameliorate the adverse effects of radiotherapy that result from the production of cellular mediators of inflammation and tissue injury. One of these mediators is TNF, which participates in a variety of physiologic processes, most notably the inflammation response that results in host defense and the deleterious effects of chronic inflammation. Clinical studies have demonstrated that TNF is released from monocytes cultured from patients receiving radiotherapy, and increased TNF serum levels in patients receiving fractionated total body irradiation prior to bone marrow transplantation. Serum concentrations of TNF correlated with the severity of interstitial pneumonitis, hepatic dysfunction and renal insufficiency in these patients (Holler et al., 1991; Bianco et al., 1991).

A radiation-induced increase in TNF protein production is also associated with increased TNF gene expression in human sarcoma and leukemia cell lines as well as human monocytes. In HL-60 human leukemia cells, TNF gene expression following radiation occurs through an increase in the rate of transcription.(Sherman et al., 1990). The finding that radiation mediated TNF gene induction is attenuated by inhibition or depletion of protein kinase C (PKC) suggests a mechanism that acts in common with the arachidonic acid metabolic pathway.

Figure 2:
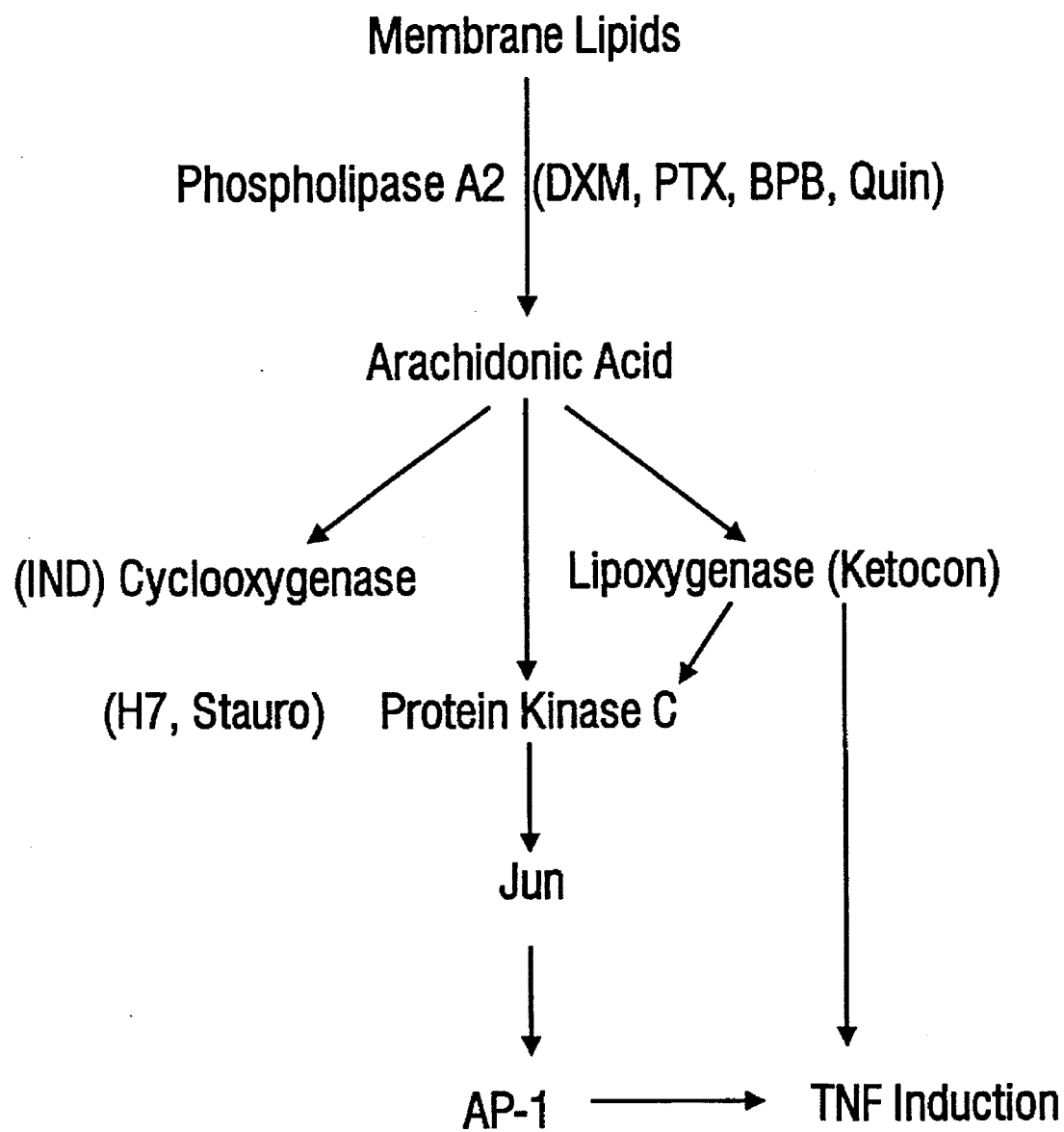
FIG. 2 Proposed signalling pathways activated by ionizing radiation. Phospholipase A2 hydrolyzes membrane lipids to form arachidonic acid which is metabolized by cyclooxygenase or lipoxygenase. Protein kinase C is subsequently activated either directly by arachidonate or indirectly through a product of lipoxygenase. Transcription factors such as c-Jun are then modified so that transcription is activated. IND=indomethacin; Ketocon=ketoconazole; DXM=dexamethasone; PTX=pentoxifylline; BPB=bromphenylbromide; Quin=quinacrine.

Phospholipase A2 is activated by $H_2O_2$ and is proposed to be one the primary mediators of reduction of oxidized membrane lipids (van Kuijk et al., 1987). Inhibition of phospholipase A2 attenuates radiation-mediated arachidonate production, PKC activation and TNF gene expression. Taken together, these findings indicate that the mechanism of arachidonate production following irradiation is most likely phospholipase A2 activation. Arachidonic acid is in turn metabolized by lipoxygenase or Cyclooxygenase. In the present study, the inventors found that inhibition of lipoxygenase attenuates radiation-induced TNF expression. However, radiation mediated Egr-1 and c-jun gene expression were not affected by ketoconazole, indicating that signal transduction through the lipoxygenase pathway is not a generalized pathway common to all radiation-inducible genes. Cyclooxygenase inhibition, however, may enhance TNF expression by reducing the production of prostaglandin E2, which acts as a negative regulator of TNF expression (Kunkel, 1988). Another possibility is that arachidonate is diverted into lipoxygenase pathway when cyclooxygenase is inhibited resulting in a greater quantity of messengers. These proposed signalling pathways activated by ionizing radiation are illustrated in FIG. 2.

The finding that quinacrine and pentoxifylline block X ray-induction of each of the radiation-inducible genes examined in this study indicates that these agents may be non-specific and inhibit multiple signalling pathways at various levels. Signal divergence through PKC-dependent and independent pathways following irradiation has been suggested in HL-525 human leukemia cells deficient in radiation-induced PKC activation (Datta et al., 1992). Radiation-induced TNF gene expression is undetectable in HL-525 cells, while c-jun and Egr-1 expression are not reduced compared to irradiated parental cells (HL-60 cells) with normal PKC activation (Datta et al. 1992, Hallahan, 1991). This is further supported by the observation that dexamethasone specifically inhibits X ray-induced TNF gene expression while not altering jun and Egr-1 induction. The biological significance is the identification of extranuclear signalling pathways have been identified in irradiated human cells. It is likely that oxidation of membrane lipids is the inciting event in this signalling pathway.

DNA-damage-independent signalling pathways have been implicated in human fibroblasts following exposure to ultraviolet, γ-rays or $H_2O_2$ (Keyes et al. 1992). Although DNA damage has been shown to be the inciting event in irradiated prokaryotes and lower eukaryotes, oxidation of other cellular organelles such as the cell membrane may be biologically significant.

Acute radiation sequelae that mimic local inflammatory reactions include pneumonitis, proctitis, mucositis, dermatitis and esophagitis. These consequences of radiotherapy may be associated with cytokines such as TNF or arachidonic acid metabolites. This view is supported by animal and clinical studies with phospholipase A2 inhibitors (glucocorticoids and pentoxifylline) which ameliorate acute radiation sequelae (Bianco et al. 1991, Phillips et al., 1975). One application of the use of cytokine inhibition is during severe mucositis in patients infected with the human immunodeficiency virus (Cooper, 1990). It is proposed that radiation-induced TNF induction and/or arachidonic acid production may contribute to this syndrome since TNF both enhances cell killing by radiation, and is a mediator of inflammation. A study that supports the hypothesis that TNF inhibition might be clinically useful are the demonstration that HIV infected human cells are sensitive to TNF cytotoxicity (Wong et al., 1991). Furthermore, the inventors have observed that mucositis immediately worsens when a course of ketoconazole is completed in some HIV infected patients receiving radiotherapy. It is suggested that lipoxygenase inhibitors may improve the therapeutic ratio in immunocompromised patients receiving radiotherapy to the oropharyngeal mucosa. Other considerations are to use pentoxifylline or glucocorticoids, as these agents also attenuate TNF induction by ionizing radiation.

Radiation Inducible Promoters

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit. Exemplary and preferred promoters are the TATA box, the CAAT box and GC-rich sequence elements.

Another type of discrete transcription regulatory sequence element is an enhancer. An enhancer provides specificity of time, location and expression level for a particular encoding region (e.g., gene). A major function of an enhancer is to increase the level of transcription of an encoding region in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. As used herein, a "radiation responsive enhancer-promoter" or "radiation inducible promoter" indicates an enhancer-promoter whose transcription controlling function is affected by ionizing radiation. Typically, upon exposure to an effective dose of ionizing radiation, a radiation responsive enhancer-promoter of the present invention stimulates or increases the rate of transcription of an encoding region controlled by that enhancer-promoter. An exemplary and preferred enhancer-promoter for use in a DNA molecule of the present invention is a CArG domain of an Egr-1 promoter, a promoter for tumor necrosis factor-alpha (TNF-α) gene or a c-Jun promoter.

a. CArG Domain of Egr-1 Promoter

Exposure of mammalian cells to ionizing radiation is associated with induction of Egr-1 gene expression. The Egr-1 gene (also known as zif/268, TIS-8, NFGI-A and Krox-24; Sukhatme, et al. 1988; Christy, et al., 1988; Milbrandt, 1987; Lemaire, et al., 1988; Lim, et al., 1987; Gessler, 1990) encodes a 533-amino acid residue nuclear phosphoprotein with a $Cys_2$-$His_2$ zinc finger domain that is partially homologous to the corresponding domain in the Wilms' tumor-susceptibility gene (Gessler, 1990). The Egr-1 protein binds to the DNA sequence CGCCCCCGC in a zinc-dependent manner and functions as a regulator of gene transcription (Christy, et al., 1989; Cao, et al., 1990; Lau, et al., 1987). Both mitogenic and differentiation signals have been shown to induce the rapid and transient expression of Egr-1 in a variety of cell types. Exposure of human HL-525 cells to x-rays was associated with increases in Egr-1 mRNA levels. Those increases were maximal at 3 hours and transient. Nuclear run-on assays demonstrated that this effect was related at least in part to activation of Egr-1 gene transcription.

Sequences responsive to ionizing radiation-induced signals were determined by deletion analysis of the Egr-1 promoter. X-ray inducibility of the Egr-1 gene was conferred by a region containing six serum response or $CC(A/T)_6GG$ (CArG) domains or domains.

A region encompassing the three distal or upstream CArG elements was functional in the x-ray response as sequential deletion of those three CArG domains progressively decreased the response. A single CArG domain, however, was found to be sufficient to confer X-ray inducibility. Those results indicate that ionizing radiation induces Egr-1 tranc-scription through one or more CArG domains.

In order to identify cis elements responsible for x-ray-induced Egr-1 transcription, the Egr-1 promoter region extending from position −957 upstream to the transcription start site to position +248 was ligated to a chloramphenicol acetyl transferase (CAT) reporter gene to form plasmid pEgr-1 P1.2 The Egr-1 promoter region contains several putative cis elements including six CArG domains (Christy, et al., 1989; Qureshi, et al., 1991). Treatment of pEgr-1 P1.2 transfected cells with ionizing radiation was associated with a 4.1-fold increase in CAT activity as compared to transfected but unirradiated cells. In contrast, similar studies performed with plasmid pΔEgr-1 P1.2 (similar to pEgr-1 P1.2 except that nucleotides from position −550 to −50 are deleted) demonstrated little if any inducibility by x-rays. Thus, x-ray inducibility of Egr-1 is likely mediated by sequences present between −550 and −50 of the Egr-1 promoter.

X-ray inducibility of the Egr-1 gene is conferred by a region of the Egr-1 promoter that contains CArG domains. The six CArG domains of the Egr-1 promoter are located within a region of the Egr-1 promoter located about 960 nucleotide bases upstream from the transcription initiation site of the Egr-1 gene (reference). A single CArG domain is sufficient to confer radiation inducibility. Preferably, a radiation responsive enhancer-promoter comprises at least one of the three most distal (i.e. upstream) CArG domains.

Studies with the c-fos promoter have demonstrated that the CArG domain or serum response element is functional in inducing transcription of this gene in response to serum and other signals (Triesman, 1990). The CArG element is required for c-fos induction by both PKC-mediated signalling pathways and by growth factor-induced signals independent of PKC (Fisch, et al., 1987; Gilman, 1988; Buscher, et al., 1988; Sheng, et al., 1988; Stumpo, et al., 1988; Graham, et al., 1991). The kinetics of induction, as well as repression, of c-fos expression are similar to those of Egr-1 in other models (Sukhatme, et al., 1988; Guis, et al., 1990). Indeed, x-ray-induced changes in c-los transcripts are similar to those obtained for Egr-1 in HL-525 cells and TPA-induced c-fos expression, like that for Egr-1, is attenuated in these cells. Studies with the c-fos promoter have demonstrated that the CArG domain functions as a binding site for the serum response factor (SRF) (Treisman, 1986; Prywes, et al., 1988). SRF binds, but with varying affinity, to the different CArG elements in the Egr-1 promoter (Christy, et al., 1989).

Previous studies have demonstrated that binding of SRF to CArG in the c-fos promoter is not detectably altered by serum and other conditions (Treisman, 1986; Prywes, et al., 1986; Sheng, et al., 1988). Nuclear proteins from quiescent and serum-stimulated 3T3 cells have also shown little if any difference in binding to the first CArG element of the Egr-1 promoter (Gius, et al., 1990). These findings suggest that ionizing radiation, like serum, induces a post transcriptional modification of SRF. Other studies have demonstrated that phosphorylation of SRF is required for activation or transcription (Prywes, et al., 1988). The kinases responsible for this effect, however, remain unclear.

Alternatively, ionizing radiation may result in the modification of other proteins that interact with the SRF or CArG domain. Both SAP-1 and p62$^{TCF}$ (ternary complex factor) recognize SRF-DNA complexes (Dalton, et al., 1992; Shaw, et al., 1989), while p62$^{DBF}$ (direct binding factor) binds directly to the SRE (Ryan, et al., 1989; Walsh, 1989). Other studies have demonstrated that SRE-ZBP undergoes post-translational modification and binds to this element (Attar, et al., 1992). One or more of these proteins may therefore be involved in x-ray-induced Egr-1 transcription.

b. c-Jun promoter

Exposure of cells to x-rays is associated with activation of the c-Jun/c-fos gene families, which encode transcription factors (Hallahan, et al., 1991; Sherman, et al., 1990).

The c-Jun gene encodes the major form of the 40–44 kD AP–1 transcription factor (Mitchell, et al., 1989). The Jun/AP-1 complex binds to the heptomeric DNA consensus sequence TGA$^G/_C$TCA (Mitchell, et al., 1989). The DNA binding domain of c-Jun is shared by a family of transcription factors, including Jun-B, Jun-D and c-fos. Moreover, the affinity of c-Jun binding to DNA is related to the formation of homodimers or heterodimers with products of the fos gene family (Zorial, et al., 1989; Nakabeppu, et al., 1988; Halazonetis, et al., 1988).

Phorbol ester activation of c-Jun transcription in diverse cell types has implicated the involvement of a protein kinase C (PKC)-dependent mechanism (Brenner, et al., 1989; Angel, et al., 1988b; Hallahan, et al., 1991a). A similar pathway likely plays a role, at least in part, in the induction of c-Jun expression by ionizing radiation. Prolonged treatment with phorbol esters to down-regulate PKC is associated with decreases in the effects of x-rays on c-Jun transcription (Hallahan, et al., 1991a). Furthermore, non-specific inhibitors of PKC, such as the isoquinolinesulfonamide derivative, H7, block x-ray-induced c-Jun gene product expression (Hallahan, et al., 1991a).

The effects of ionizing radiation on c-jun gene product expression were studied in an HL-60 cell variant, designated HL-525, which variant is deficient in PKC-mediated signal transduction (Homma, et al., 1986). That variant is resistant to both phorbol ester-induced differentiation and x-ray-induced TNF gene product expression (Hallahan, et al., 1991b; Homma, et al., 1986) and resistant to the induction of c-jun gene product expression by phorbol esters.

Treatment of those cells with ionizing radiation was associated with a superinduction of c-Jun mRNA levels compared to phorbol ester-responsive HL-60 cells. Transcription of c-Jun was low in untreated HL-525 cells. However, exposure of those cells to ionizing radiation resulted in c-Jun mRNA levels which were substantially higher at 3, 6 and 8 hours after x-ray exposure than in non-irradiated cells. Expression of the Jun-B and Jun-D gene products was also transiently increased following x-irradiation of the HL-525 cells. The kinetics of those increases in los gene product expression were similar to that obtained for members of the Jun gene family.

The activation of Jun likely results in increased transcription of the AP-1 binding site following ionizing radiation exposure. The plasmid p3xTRE-CAT (containing three AP-1 sites upstream of the minimal tk promoter from plasmid pBLCAT2) was transfected into RIT-3 cells. Irradiation of p3xTRE-CAT transfectants resulted in a 3-fold increase in CAT expression.

Where RIT-3 cells transfected with a DNA molecule (c-Jun-CAT) comprising a 1840-base pair (−1.1 kb to +740 bp) segment of the c-Jun promoter placed upstream of the CAT gene were exposed to ionizing radiation, CAT expression increased about 3-fold relative to transfected, non-irradiated cells. Transfection of those cells with a plasmid having a deletion of the AP-1 site located at +150-bp (−132/+170 Δ AP-1CAT) resulted in a loss of x-ray-mediated induction of CAT expression. Thus, activated AP-1 likely participates in the transcription of c-Jun and the AP-1 DNA sequence is likely sufficient and necessary to confer x-ray-mediated c-Jun gene induction.

Because X-ray induced c-Jun gene expression is attenuated when PKC is depleted or inhibited, the PKC inhibitor H7 was added to RIT-3 cells transfected with pSG-Jun5-235 and G5BCAT. H7 treatment abrogated the x-ray induced increase in CAT activity suggesting that irradiation induced PKC activation is required for gene expression (Hallahan, 1991a; Hallahan, 1991b). These data suggest that dissociation from the Jun inhibitor may be one mechanism of regulating radiation-mediated transcription.

c. TNF-α promoter

Tumor necrosis factor α (TNF-α) is a polypeptide mediator of the cellular immune response with pleiotropic activity. TNF-α acts directly on vascular endothelium to increase the adhesion of leukocytes during the inflammatory process (Bevelacqua, et al., 1989). This in vivo response to TNF-α was suggested to be responsible for hemorrhagic necrosis and regression of transplantable mouse and human tumors (Carswell, 1975). TNF-α also has a direct effect on human cancer cell lines in vitro, resulting in cell death and growth inhibition (Sugarman, et al., 1985; Old, 1985). The cytotoxic effect of TNF-α correlates with free-radical formation, DNA fragmentation, and microtubule destruction (Matthews, et al., 1988; Rubin, et al., 1988; Scanlon, et al., 1989; Yamauchi, et al., 1989; Matthews, et al., 1987; Neale, et al., 1988). Cell lines that are resistant to oxidative damage by TNF-α also have elevated free-radical buffering capacity (Zimmerman, et al., 1989; Wong, et al., 1988).

In addition, TNF-α causes hydroxyl radical production in cells sensitive to killing by TNF-α (Matthews, et al., 1987). Cell lines sensitive to the oxidative damage produced by TNF-α have diminished radical-buffering capacity after TNF-α is added (Yamauchi, et al., 1989). Lower levels of hydroxyl radicals have been measured in cells resistant to TNF-α cytotoxicity when compared with cells sensitive to TNF-α killing (Matthews, et al., 1987).

TNF-α is increased after treatment with x-rays in certain human sarcoma cells (e.g., STSAR-13 and STSAR-48). TNF-α mRNA levels were substantially elevated 3 and 6 hours after irradiation of STSAR-13 and STSAR-48 cells. TNF-α mRNA levels in cell line STSAR-13 increased by >2.5-fold as measured by densitometry 3 hours after exposure to 500 cGy and then declined to baseline levels by 6 hours. TNF-α transcripts increased at 6 hours after irradiation in cell line STSAR-48, thus indicating some heterogeneity between cell lines in terms of the kinetics of TNF-α gene expression. In contrast, irradiation had no detectable effect on 7S RNA levels or expression of the polymerase β gene.

The increase in TNF-α mRNA was accompanied by an increased expression of TNF-α protein, which increase was accompanied by secretion of TNF-α protein into the medium in which those cells were grown. Levels of TNF-α in the medium of human tumor cell lines and fibroblasts were quantified before and after exposure to ionizing radiation. Five of 13 human bone and soft tissue sarcoma cell lines (STSAR-5, -13, -33, -43, and -48) released TNF-α into the medium after irradiation, whereas TNF-α levels were not elevated in supernatant from normal human fibroblast cell lines (GM-1522 and NHF-235) and four human epithelial tumor cell lines (HN-SCC-68, SCC-61, SCC-25, and SQ-20 B) after exposure to radiation. Tumor cell line STSAR-13 produced undetectable amounts of TNF-α before x-irradiation and 0.35 units/ml after x-ray exposure. Cell lines STSAR-5 and -33 responded to x-irradiation with increases in TNF-α concentrations of >5-to 10 fold. Cell lines STSAR-43 and -48 demonstrated increases in TNF-α of 1.5- to 3-fold. TNF-α protein in the medium was first elevated at 20 hr after x-ray treatment, reached maximal levels at 3 days, and remained elevated beyond 5 days. Furthermore, supernatant from irradiated, but not control STSAR-33 cells, was cytotoxic to TNF-α-sensitive cell line SQ-20B.

2. Encoding Region

A radiation responsive enhancer-promoter is operatively linked to an encoding region that encodes at least one polypeptide. As used herein, the phrase "operatively linked" means that an enhancer-promoter is connected to an encoding region in such a way that the transcription of that encoding region is controlled and regulated by that enhancer-promoter. Means for operatively linking an enhancer-promoter to an encoding region are well known in the art. As is also well known in the art, the precise orientation and location relative to an encoding region whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

a. Single polypeptide

In one embodiment, an encoding region of a DNA molecule of the present invention encodes a single polypeptide. As used herein, the term "polypeptide" means a polymer of amino acids connected by amide linkages, wherein the number of amino acid residues can range from about 5 to about one million. Preferably, a polypeptide has from about 10 to about 1000 amino acid residues and, even more preferably from about 20 to about 500 amino residues. Thus, as used herein, a polypeptide includes what is often referred to in the art as an oligopeptide (5–10 amino acid residues), a polypeptide (11–100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Any polypeptide can be encoded by an encoding region of a DNA molecule of the present invention. An encoding region can comprise introns and exons so long as the encoding region comprises at least one open reading frame for transcription, translation and expression of that polypeptide. Thus, an encoding region can comprise a gene, a split gene or a cDNA molecule. In the event that the encoding region comprises a split gene (contains one or more introns), a cell transformed or transfected with a DNA molecule containing that split gene must have means for removing those introns and splicing together the exons in the RNA transcript from that DNA molecule if expression of that gene product is desired.

In a preferred embodiment, a polypeptide encoded by an encoding region of a DNA molecule of the present invention interferes with the structural or functional integrity of a cell exposed to that polypeptide. Such a polypeptide has the ability to inhibit the growth of a cell and, particularly a tumor cell. A polypeptide is preferably a cytokine, a dominant negative, a tumor suppressing factor, an angiogenesis inhibitor, a radioprotective peptide, radiosensitizing peptide, or a monocyte chemoattractant.

Dominant negatives to cellular enzymes such as Raf-1 kinase are cytotoxic to human tumor cells (Qureshi, et al., 1991). Dominant negatives to oncogenes such as N-myc may also be effective in the treatment of cancer.

Expression of tumor suppressor genes such as p53, the retinoblastoma (Rb) susceptibility gene, Wilms' tumor gene can be controlled by radiation. Transfection of p53 deficient tumor cells with a p53 expression vector abrogates cell growth (Johnson, et al., 1991).

Tumor growth is angiogenesis-dependent and angiogenesis is directly or indirectly induced by the tumor. Induction of anglogenesis is an important step in carcinogenesis and in metastatic development. Angiogenesis is induced during the transition from hyperplasia to neoplasia. Since angiogenesis is necessary for tumor growth, any natural or synthetic antiangiogenic compound may have an antineoplastic potential. Inhibition of tumor angiogenesis through controlled expression of an anti-angiogenesis gene could play an important role in cancer treatment. Inhibitors of capillary endothelial cell proliferation and/or angiogenesis are a cartilage-derived inhibitor and platelet factor 4 (PF4) (reviewed in Neta, et al., 1991; Zucker, et al., 1991).

The mouse fibroblast gene is induced by PDGF. The fibroblast gene product, JE or monocyte chemoattractant protein-1 (MCP-1) is a member of a family of cytokine-like glycoproteins whose expression is induced by a mitogenic signal in monocytes, macrophages and T cells. JE has been identified, characterized and recombinantly produced from both mouse and human fibroblasts (Rollins et al., 1989). The mouse and human fibroblast gene products are designated mJE and hJE, respectively.

MCP-1 or JE is a monocyte-specific chemoattractant in vitro that is structurally related to a family of proinflammatory cytokines such as macrophage inflammatory proteins.

Exemplary and preferred polypeptides are interleukin-4, JE, PF4 ricin, a bacterial toxin such as Pseudomonas toxin; p53, the retinoblastoma gene product or the Wilms' tumor gene product.

In another preferred embodiment a polypeptide encoded by an encoding region has radioprotective activity toward normal cells (i.e., the polypeptide protects a normal cell or tissue from a deleterious effect of radiation). Exemplary and preferred polypeptides having radioprotective activity are interleukin-1; tumor necrosis factor; a tissue growth factor such as a hematopoietic growth factor, a hepatocyte growth factor, a kidney growth factor, an endothelial growth factor or a vascular smooth muscle growth factor; interleukin-6, a free radical scavenger or a tissue growth factor receptor.

Preferably, 1) a hematopoietic growth factor is a colony stimulating factor such as GM-CSF, G-CSF, M-CSF or interleukin-3; 2) an endothelial growth factor is basic fibroblast growth factor; 3) a vascular smooth muscle growth factor is platelet derived growth factor (PDGF); and 4) a free radical scavenger is manganese superoxide dismutase (MnSOD).

The radioprotective effect of administered IL-1 and IL-6 have been demonstrated (Neta, et al., 1991; Neta, et al., 1992). The added benefit of radioprotection of hematopoietic cells was demonstrated by exogenous TNF added prior to irradiation which has been demonstrated to protect the hematopoietic system in animals (Neta, et al., 1991).

Studies by Neta et al have demonstrated that IL-1 induces several hematopoietic growth factors (GM-CSF, G-CSF, M-CSF, IL 3, and IL 6) which clearly contribute to the accelerated growth and differentiation of hematopoietic progenitor cells (Neta, et al, 1991). Uckun et al have examined the radioprotective effects of pre-total body irradiation (TBI) conditioning with recombinant granulocyte colony-stimulating factor (rG-CSF) and recombinant granulocyte-macrophage CSF (rGM-CSF) in a large series of lethally irradiated mice (Uckun, et al, 1989). Administration of rG-CSF or rGM-CSF before TBI protects a significant fraction of mice from the lethal effects of LD 100/30 TBI (Waddick, et al., 1991). At equivalent doses, rG-CSF displayed a more potent radioprotective activity than rGM-CSF. The survival rate after lethal TBI was also significantly higher in mice receiving optimally radioprotective doses of rG-CSF as compared with mice receiving optimally radioprotective doses of rGM-CSF. Pretreatment with rG-CSF followed by rGM-CSF was slightly more effective than rG-CSF alone in supralethally irradiated mice but not in lethally irradiated mice. Neta et al. have also shown that administration of suboptimal, nonradioprotective doses of IL-1 alpha also synergize with GM-CSF or G-CSF to confer optimal radioprotection (Neta, et al., 1988), suggesting that such an interaction may be necessary for radioprotection of hemopoietic progenitor cells.

In still yet another preferred embodiment, a polypeptide encoded by an encoding region has the ability to catalyze the conversion of a pro-drug to a drug or to sensitize a cell to a therapeutic agent. By way of example, cells manipulated to contain a herpes simplex virus (HSV) gene for thymidine kinase (tk) and to express HSV-tk become sensitive to the action of the antiviral agent ganciclovir (GCV) (Culver et al., 1992). By way of further example, cells manipulated to contain a gene for bacterial cytosine deaminase and to express that enzyme can catalyze the conversion of inactive, non-toxic 5'-fluorocytosine to the active cytotoxin 5-fluorouracil (Culver et al., 1992).

Thus, a preferred polypeptide that has the ability to catalyze the conversion of a pro-drug to a drug or to sensitize a cell to a therapeutic agent is herpes simplex virus thymidine kinase or a cytosine deaminase.

A further preferred polypeptide encoded by an encoding region is a surface antigen that is a gene product of a major histocompatibility complex (MHC). As is well known in the art, MHC represents a set of linked genetic loci involved in regulating the immune response. MHC gene products occur on cell surfaces where they act as antigenic markers for distinguishing self from non-self. Typically, MHC gene products are classified as being of a class I or Class II depending upon their function. MHCs from different animals have been given different and corresponding designations. By way of example, human MHC gene products are designated by the prefix HL; mouse MHC gene products are designated by the prefix H-2; rat MHC gene products are designated by the prefix RT1 and chimpanzee MHC gene products are designated by the prefix ChLA.

Exemplary and preferred human MHC gene products are class I antigens HLA-A, HLA-B and HLA-D and class II antigens HLA-Dr and HLA-Dc.

b. More than one polypeptide

In another aspect, an encoding region of a DNA molecule of the present invention encodes the whole or a portion of more than one polypeptide. Preferably, those polypeptides are transcription factors.

A transcription factor is a regulatory protein that binds to a specific DNA sequence (e.g., promoters and enhancers) and regulates transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

Where a DNA fragment is obtained from a cell or other organism, total DNA is extracted from that organism or cell and fragmented using restriction enzymes. The choice of what restriction enzyme or enzymes to use is dependent upon the desired DNA sequence being obtained. Particular DNA sequences of interest are then isolated, identified and purified using standard techniques well known in the art. If needed, an encoding DNA sequence can be amplified prior to isolation. A preferred means of amplifying a DNA sequence of interest is the polymerase chain reaction.

3. Preparation of a DNA Molecule

A DNA molecule of the present invention is prepared in accordance with standard techniques well known to a skilled worker in the art. First, DNA fragments containing the various regions of a desired DNA molecule are prepared or isolated. Those regions are then ligated to form a DNA molecule of this invention. Means for synthesizing, isolating and ligating DNA fragments are well known in the art.

DNA sequences of up to about 200 base pairs can be prepared using well known solid phase synthetic techniques. Thus, by way of example, where a radiation responsive enhancer-promoter is a CArG domain of an Egr-1 promoter, one or more of that domain can be synthetically prepared.

Where a desired DNA sequence is of about 200 or more nucleotides, that sequence is typically obtained from tissues, cells or commercially available constructs (e.g. vectors or plasmids) known to contain that desired sequence. Other DNA molecules of the present invention are made using techniques similar to those set forth above.

Pharmaceutical Compositions

In another aspect, the present invention contemplates a pharmaceutical composition comprising an inhibitor of lipoxygenase in a therapeutically effective amount and a physiologically acceptable carrier. Also contemplated is a therapeutically effective amount of at least one DNA molecule of the present invention and a physiologically acceptable carrier.

A therapeutically effective amount of an inhibitor of lipoxygenase or a DNA molecule that is combined with a carrier to produce a single dosage form varies depending upon the host treated and the particular mode of administration.

As is well known in the art, a specific dose level for any particular patient depends upon a variety of factors including the activity of the specific compound employed, the age, body weight, general health, sex, diet, time of administration, route of administration, rate of excretion, drug combination, and the severity of the particular disease undergoing therapy.

A composition of the present invention is typically administered orally or parenterally in dosage unit formulations containing standard, well known nontoxic physiologically acceptable carriers, adjuvants, and vehicles as desired. The term parenteral as used herein includes subcutaneous injections, intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

A DNA molecule of the present invention can also be complexed with a poly(L-Lysine)(PLL)-protein conjugate such as a transferrin-PLL conjugate or an asialoorosomucoid-PLL conjugate.

Liquid dosage forms for oral administration include pharmaceutically acceptable emulsions, syrups, solutions, suspensions, and elixirs containing inert diluents commonly used in the art, such as water. Such compositions can also comprise adjuvants, such as wetting agents, emulsifying and suspending agents, and sweetening, flavoring, and perfuming agents.

In another aspect, the present invention provides a cell transformed or transfected with one or more DNA molecules of the present invention as well as transgenic cells derived from those transformed or transfected cells. Means of transforming or transfecting cells with exogenous DNA molecules are well known in the art.

A DNA molecule is introduced into a cell using standard transformation or transfection techniques well known in the art such as calcium-phosphate- or DEAE-dextran-mediated transfection, protoblast fusion, electroporation, liposomes and direct microinjection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transferred to the nucleus. Depending on the cell type, up to 20% of a population of cultured cells can be transfected at any one time. Because of its high efficiency, transfection mediated by calcium phosphate or DEAE-dextran is the method of choice for studies that require transient expression of the foreign DNA in large numbers of cells. Calcium phosphate-mediated transfection is also used to establish cell lines that carry integrated copies of the foreign DNA, which are usually arranged in head-to-tail tandem arrays.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandomly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transformation involves encapsulation of DNA and RNA within liposomes, followed by fusion of the liposomes with the cell membrane. In addition, DNA that is coated with a synthetic cationic lipid can be introduced into cells by fusion.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

Process of Regulating Expression

In another aspect, the present invention contemplates a process of regulating the expression of a polypeptide. Polypeptide expression is regulated by stimulating or inhibiting transcription of an encoding region that encodes that polypeptide. In accordance with one embodiment, a process of regulating polypeptide expression comprises the steps of: first, operatively linking a radiation responsive enhancer-promoter to an encoding region that encodes that polypeptide, which encoding region is operatively linked to a transcription-terminating region to form a DNA molecule, and second, exposing the DNA molecule to an effective expression-inducing dose of ionizing radiation.

A DNA molecule used with such a method is a DNA molecule of the present invention as set forth above.

As used herein, the phrase "effective expression-inducing dose of ionizing radiation" means that dose of ionizing radiation needed to stimulate or turn on a radiation responsive enhancer-promoter of the present invention. The amount of ionizing radiation needed in a given cell depends generally upon the nature of that cell. Typically, an effective expression-inducing dose is less than a dose of ionizing radiation that causes cell damage or death directly. Means for determining an effective expression inducing amount are well known in the art.

In a preferred embodiment an effective expression inducing amount is from about 2 to about 20 Gray (Gy) administered at a rate of from about 0.5 to about 2 Gy/minute. Even more preferably, an effective expression inducing amount of ionizing radiation is from about 5 to about 15 Gy.

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

Cells containing a DNA molecule of the present invention encoding a particular polypeptide express that polypeptide when exposed to ionizing radiation.

As used herein, the term "irradiated cell" means a cell or tissue that has been exposed to an effective expression-inducing dose of ionizing radiation that stimulates or turns on a radiation responsive enhancer-promoter of the present invention and depends on the given cell type.

By way of example, treatment of cells transfected with plasmid pEgr-1P1.2 with ionizing radiation was associated with a 4.1-fold increase in CAT activity as compared to transfected but unirradiated cells. Plasmid pEgr-1 P1.2 comprises a radiation responsive enhancer-promoter (the Egr-1 promoter region extending from position -957 upstream to the transcription start site to position +248) operatively linked to the CAT reporter gene. Indeed, irradiation of pE425-CAT transfected cells was associated with a 3.6-fold induction of CAT activity compared to that in non-irradiated cells transfected with this construct.

By way of further example, TNF-α protein expression was induced by ionizing radiation in cells transfected with plasmid pE425-TNF. SQ-20B, RIT-3 and HL-525 cells were transfected with plasmid pE425-TNF by DEAE precipitation. Transfected cells were exposed to 10 Gy of x-radiation at a rate of 1 Gy/minute. TNF-α expression was increased about 2-fold, 5-fold and 4-fold, respectively in SQ-20B, RIT-3 and HL-525 cells when compared to transfected, non-irradiated cells.

By way of still further example, CAT expression was induced by ionizing radiation in RIT-3 cells transfected with plasmid c-Jun-CAT, which plasmid comprises a 1100 base pair segment of the c-Jun promoter operatively linked to a CAT gene. Cells were cotransfected with an SV40 promoter-β galactosidase expression vector to control for transfection efficiency.

Transfectants were irradiated (10 Gy, 1 Gy/min, GE Maxitron) 40 hours after transfection. CAT was extracted 6 hours after irradiation. CAT activity increased about 3-fold following irradiation of RIT-3 cells transfected with pc-Jun-CAT. β gal expression was not affected by radiation. Ionizing radiation did not increase CAT expression in cells transfected with a plasmid comprising the minimal Jun promoter (nucleotide base position-18 to nucleotide base position +170 relative to the transcription start site) operatively linked to CAT.

These data show that ionizing radiation can be used as a trigger to regulate transcription of an encoding region in a DNA molecule of the present invention and expression of a polypeptide encoded by that region.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Inhibition of TNF by Phospholipase and Lipoxygenase Inhibitors

Cell Line

HL-60 cells were maintained in RPMI medium and 20% fetal bovine serum (FBS), 100 units/ml penicillin and 100 µg/ml streptomycin. During survival analysis, the colony forming assay was used and cells were cultured in semisolid medium consisting of 0.8% methylcellulose in RPMI and 20% fetal calf serum. Pentoxifylline (3,7-dimethyl-1-(5-oxo-hexyl)-xanthine), dexamethasone 1 µM, quinacrine, ketoconazole, or indomethacin were each added to cultures one hr prior to irradiation.

RNA Analysis Following Irradiation

HL-60 cells were serum deprived for 24 hrs. Cells were exposed to 10 Gy as previously described (Hallahan et al., 1989). Pentoxifylline (1 mM) was added to cell cultures 1 hr prior to irradiation with 10 Gy. RNA was extracted at 1 hr following irradiation using the single step guanidinium thiocyanate-phenol/chloroform method (Chomczynski et al., 1987). Control RNA from nonirradiated cells treated with otherwise identical conditions and RNA from irradiated cells was size fractionated by 1% agarose formaldehyde electrophoresis. Ethidium bromide staining of the RNA demonstrated equal loading of each lane. RNA gels were then transferred to a nylon membrane. Northern blots were hybridized to $^{32}$P labeled TNF, Egr-1 and c-jun cDNA probes (Cao et al., 1990, Hatori et al., 1988, Spriggs et al., 1990), followed by autoradiography for 3 days at −85° C. with intensifying screens.

Results

Figure 1:
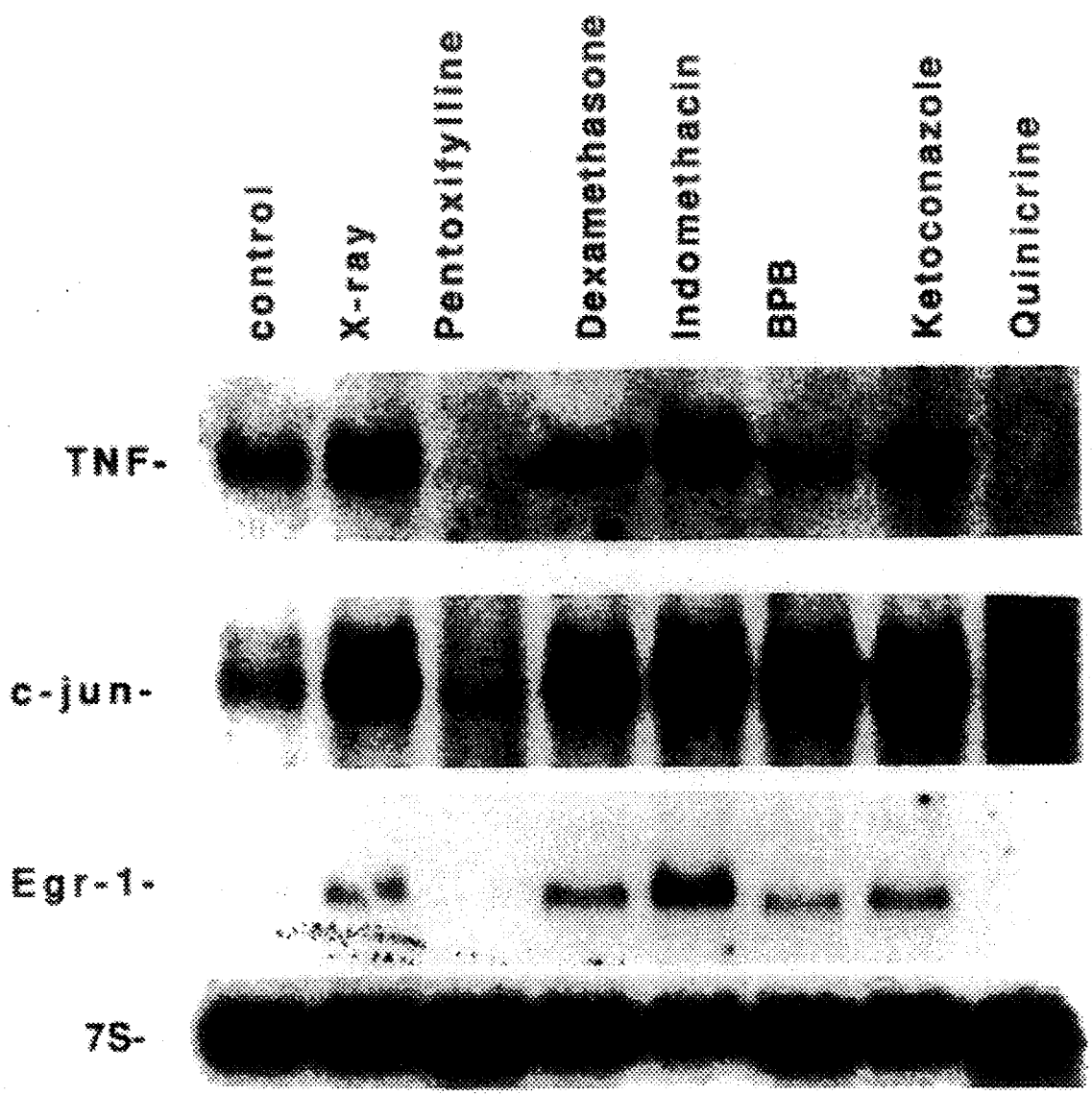
FIG. 1 HL-60 cells were pretreated with ketoconazole, indomethacin, U7 or no drug (x-ray alone) followed by irradiation. RNA was isolated, separated by electrophoresis and transferred to Northern blots. Blots were then hybridized to the cDNA from Egr-1, c-jun and TNF. Gene expression is compared to that of untreated control cells. 7S hybridization demonstrates equal loading of lanes.

It has been demonstrated that the phospholipase A2 inhibitors pentoxifylline, dexamethasone, and bromphenyl-bromide attenuate radiation-mediated arachidonate production, PKC activation and TNF gene expression when added to HL-60 cells 1 hour prior to irradiation. To further assess the association between phospholipase A2 activity and radiation-mediated TNF induction, the potent phospholipase A2 inhibitor quinacrine was added to HL-60 cells 1h prior to irradiation. This agent abolished TNF expression (FIG. 1). Because arachidonate may activate PKC directly or through a metabolite, inhibitors of cyclooxygenase (indomethacin) and lipoxygenase (ketoconazole) were added 1 hour prior to irradiation. Indomethacin enhanced the expression of TNF (FIG. 1) indicating that cyclooxygenase metabolites are not required for radiation-mediated TNF induction. To determine whether the lipoxygenase pathway is required for TNF induction, ketoconazole was added prior to irradiation. Ketoconazole abolished radiation-mediated TNF induction suggesting that the lipoxygenase pathway participates in the signalling pathway leading to TNF induction.

To determine whether the inhibition of gene expression by phospholipase A2 inhibitors was specific for TNF, the same Northern blots were probed with cDNAs from the radiation-inducible genes c-jun and Egr-1. C-jun and Egr-1 are regulated by both PKC-dependent and -independent signalling pathways (Datta et al., 1992). FIG. 1 shows that radiation-induced Egr-1 and c-jun gene expression was attenuated when cells were pretreated with quinacrine or pentoxifylline. In contrast, dexamethasone attenuated the induction of TNF, but not Egr-1 and c-jun expression following x-irradiation. Indomethacin enhanced radiation-induced c-jun and Egr-1 expression as it did for TNF, while ketoconazole did not attenuate Egr-1 or c-jun induction. These findings suggest that the participation of the lipoxygenase pathway in radiation-mediated gene expression is not generalized to other radiation inducible genes.

EXAMPLE II

Figure 3:
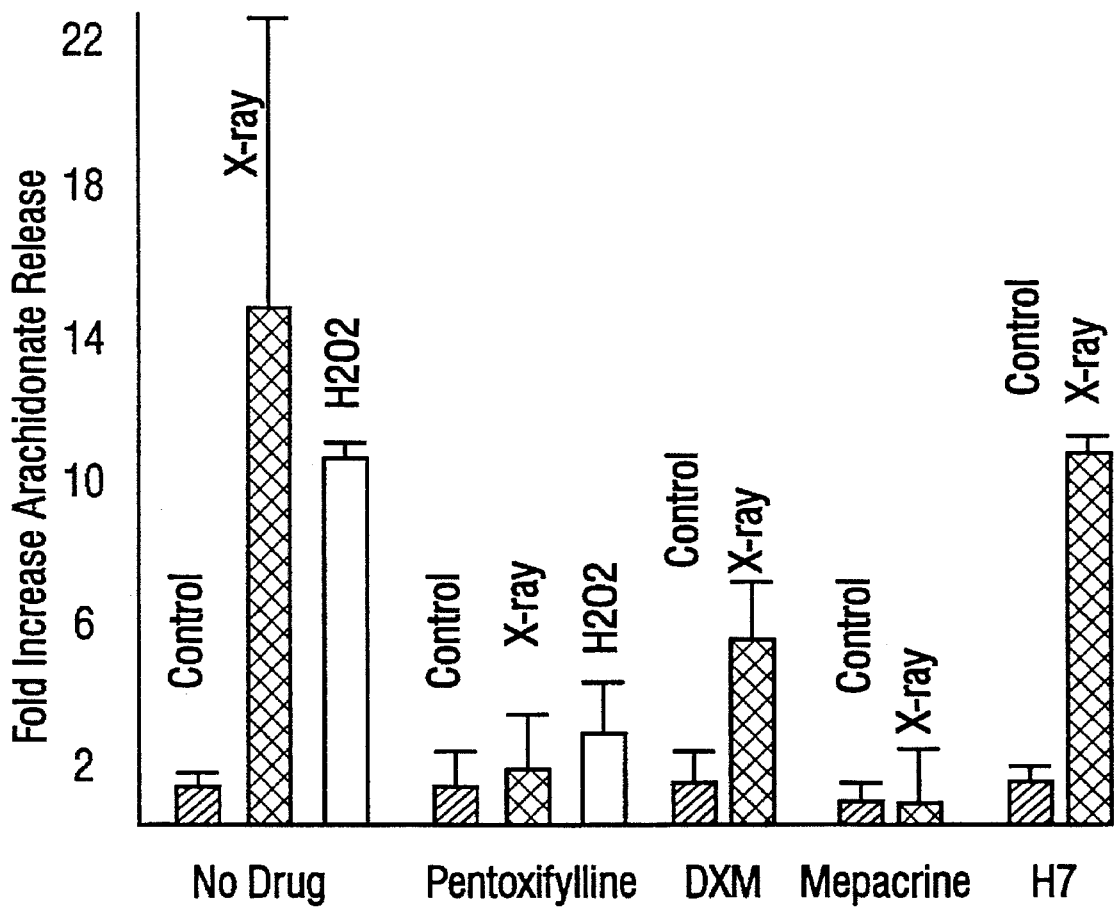
FIG. 3 Arachidonic acid release following treatment of HL-60 cells with X-rays and $H_2O_2$. HL-60 cells in logarithmic growth were incubated for 16 h in RPMI 640 medium supplemented with 1.0 mg/ml fatty acid free bovine serum albumin and 0.2 µCi/ml [$^3$H] arachidonic acid as described (24,25). Mepacrine 20 µM, BPB 10 µM, Dexamethasone 1 µM, or pentoxifylline (3,7-dimethyl-1-(5-oxo-hexyl)-xanthine, Hoffman-La Roche, Basel, Switzerland) 1 mM were added to labeled cells 1 hr prior to irradiation with 10 Gy at 1 Gy/min. At the indicated times, a 1 ml aliquot of supernatant was assayed by the addition of Hydrofluor and scintillation counting. Studies were performed 3 to 4 times and results are presented as the mean ± standard error.

The Effects of the Phospholipase A2 Inhibitors on Radiation-Induced Fatty Acid Hydrolysis Arachidonic Acid Assay HL-60 cells in logarithmic growth were incubated for 16 h in RPMI 640 medium supplemented with 1.0 mg/ml fatty acid free bovine serum albumin and 0.2 uCi/ml [$^3$H] arachidonic acid as described (Spriggs et al., 1990, Godfrey et al., 1987). Mepacrine 20 µM, BPB 10 µM, dexamethasone 1 µM, or pentoxifylline (3,7-dimethyl-1-(5-oxo-hexyl)-xanthine, Hoffman-La Roche, Basel, Switzerland) 1 mM were added to labeled cells 1 hr prior to irradiation with 10 Gy at 1 Gy/min. At the indicated times, a 1 ml aliquot of supernatant was assayed by the addition of Hydrofluor™ and scintillation counting. Studies were performed 3 to 4 times and results in FIG. 3 are presented as the mean ± standard error.

DAG kinase assay

DAG release from irradiated cells was quantified as previously described (Wright et al., 1988). Serum deprived HL-60 cells were pelleted and irradiated (10 Gy at 2.5 Gy/sec) and 100% methanol was added immediately on ice. Extracts were dried under $N_2$ and resuspended into cardiolipin and n-octylglucoside and bacterial DAG kinase in the presence of $^{32}$P-ATP. Cellular DAG was quantified by using a known concentration of synthetic DAG reacted with DAG kinase. Bradykinin was used as a positive control and resulted in a 3.0±0.4 fold increase in DAG, while x-irradiation produced DAG levels 1.2±0.4 as compared to untreated controls.

Assay of protein kinase C activity

AT cells were grown to confluence and serum deprived for 24 hours. Medium was aspirated, cells were washed with PBS and then γ-irradiated with 10.8 Gy using a Cobalt-60 source (Gammacell 220) at a dose rate of 2.7 Gy/second. Protein was extracted on ice at 15 second intervals following irradiation by the addition of 0.4 ml of lysis buffer (20 µM Tris/HCl, pH 7.5, 0.5 mM EDTA, 0.5 mM EGTA, and 2-mercaptoethanol 10 mM (TEM) with 0.5% Triton X-100, and 25 µg/ml each leupeptin and aprotinin). Cells were homogenized and protein was partially purified as previously described (Hallahan et al., 1990b). Protein extract (25 µl) was added to 25 µof TEM, 5 µl of phospholipid (2.8 mg/ml phosphatidyl serine and 10 mM phorbol ester in Triton X-100 mixed micelles, GIBCO) (Yasuda et al., 1990) and 10 µl of $^{32}$P-ATP/substrate containing 5×10$^7$ CPM/ml of $^{32}$P-ATP (New England Nuclear), 100 µM ATP, 250 µM synthetic peptide Gln-Lys-Arg-Pro-Ser(8)- Gln-Arg-Ser-Lys-Tyr-Leu, 5 mM CaCl, 100 mM MgCl$_2$ (GIBCO) (Yasuda et al., 1990) in 20 mM Tris HCl, pH 7.5. Following incubation for 5 min at 30° C., samples were dried on phosphocellulose and washed in 1% $H_3PO_4$ twice for 5 minutes followed by washing in $H_2O$ twice for 5 min. Scintillation counts of each sample and 10 µl of unwashed $^{32}$P-ATP/substrate were performed. To calculate the rate of $^{32}$P incorporation into the peptide substrate, 100 µM of synthetic PKC specific inhibitor peptide (Arg-Phe-Ala-Arg-Lys-Gly-Ala- Leu-Arg-Gln-Lys-Asn-Val-His-Glu-Val- Lys-Asn) (GIBCO) (House et al., 1989) in 20 mM Tris 7.5 was added to PKC assays prior to 32P-ATP/substrate and samples were incubated, washed and counted as described above. Background $^{32}$P incorporation was subtracted from that of assays without inhibitor and the rate of $^{32}$P incorporated into the peptide substrate was calculated (pmol/min) as previously described (Hallahan et al., 1990b, Yasuda et al., 1990). Phosphorylation rates were normalized to 10$^6$ cells per assay.

To determine the effects of PLA2 inhibitors on radiation-mediated PKC activation, mepacrine, BPB, dexamethasone or pentoxifylline were added to HL-60 cell cultures 1 hr prior to γ-irradiated with 10.8 Gy using a Cobalt-60 source (Gammacell 220) at a dose rate of 2.7 Gy/second. Cells were placed on ice and lysis buffer was added at 60 seconds following irradiation (Hallahan et al., 1991b). Phosphotransferase activity was assayed as previously described above. Phosphorylation rates were normalized to 10$^6$ cells per assay. Studies were performed 3 times and results are presented as the mean ± standard error.

RNA analysis

Cells were grown to a density of 10$^6$/ml and exposed to 10 Gy (GE Maxitron™ X-ray generator) as previously described (Hallahan et al., 1989). RNA was extracted using the single step guanidinium thiocyanate-phenol/chloroform method (Chomczynski et al., 1987) at 1 hour following irradiation. Control RNA from nonirradiated cells treated with otherwise identical conditions and RNA from irradiated cells was size fractionated by 1% agarose formaldehyde electrophoresis. Ethidium bromide staining of the RNA demonstrated equal loading of each lane. RNA gels were then transferred to a nylon membrane (Genescreen Plus™, New England Nuclear). Northern blots were hybridized to the $^{32}$P labeled TNF cDNA probe (Spriggs et al., 1990) followed by autoradiography for 3 days at −85° C. with intensifying screens. 7S RNA hybridization was used to demonstrate equal loading of lanes. Mepacrine, dexamethasone, BPB, or pentoxifylline were added to HL-60 cell cultures 1 hr prior to irradiation with 10 Gy (1 Gy/min) using a GE Maxitron generator.

RESULTS

Arachidonic acid production was quantified in irradiated HL-60 cells which have served as a model for the study of radiation-mediated TNF gene induction and PKC-dependent signal transduction (Hallahan et al., 1991b). HL-60 cells were incubated with [³H] arachidonic acid for 3 hours, washed, irradiated with 10 Gy at 1 Gy/min. Fatty acid release into the medium was significantly increased following irradiation. Previous work has also shown that arachidonic acid release is increased following treatment with $H_2O_2$ (Gustafson et al., 1991, Shasby et al., 1988), which served as a positive control. To confirm that arachidonate was produced, the inventors performed gas chromatographic analysis of lipids extracted from irradiated HL-60 cells. Using this approach, an increase in arachidonate was detectable at 30 minutes following irradiation. Conversely, Diacylglycerol levels did not change following irradiation as determined by the DAG kinase assay.

The effects of the phospholipase A2 inhibitors mepacrine, bromphenylbromide (BPB) dexamethasone, and pentoxifylline on radiation-induced fatty acid hydrolysis were studied. Each attenuated arachidonic acid release into the medium of cells treated with X-rays or $H_2O_2$ (FIG. 3). Since PKC has been shown to activate phospholipase-mediated hydrolysis of membrane phospholipids (Godson et al., 1990, Sporn et al., 1990), the PKC inhibitor H7 was added to determine whether PKC activation contributes to lipid hydrolysis following irradiation. H7 pretreatment had no detectable effect on arachidonic acid release following irradiation of HL-60 cells (FIG. 3). This is consistent with the finding that PKC inhibition produced no reduction in arachidonic acid release following $H_2O_2$ treatment (Sporn et al., 1990).

Figure 4:
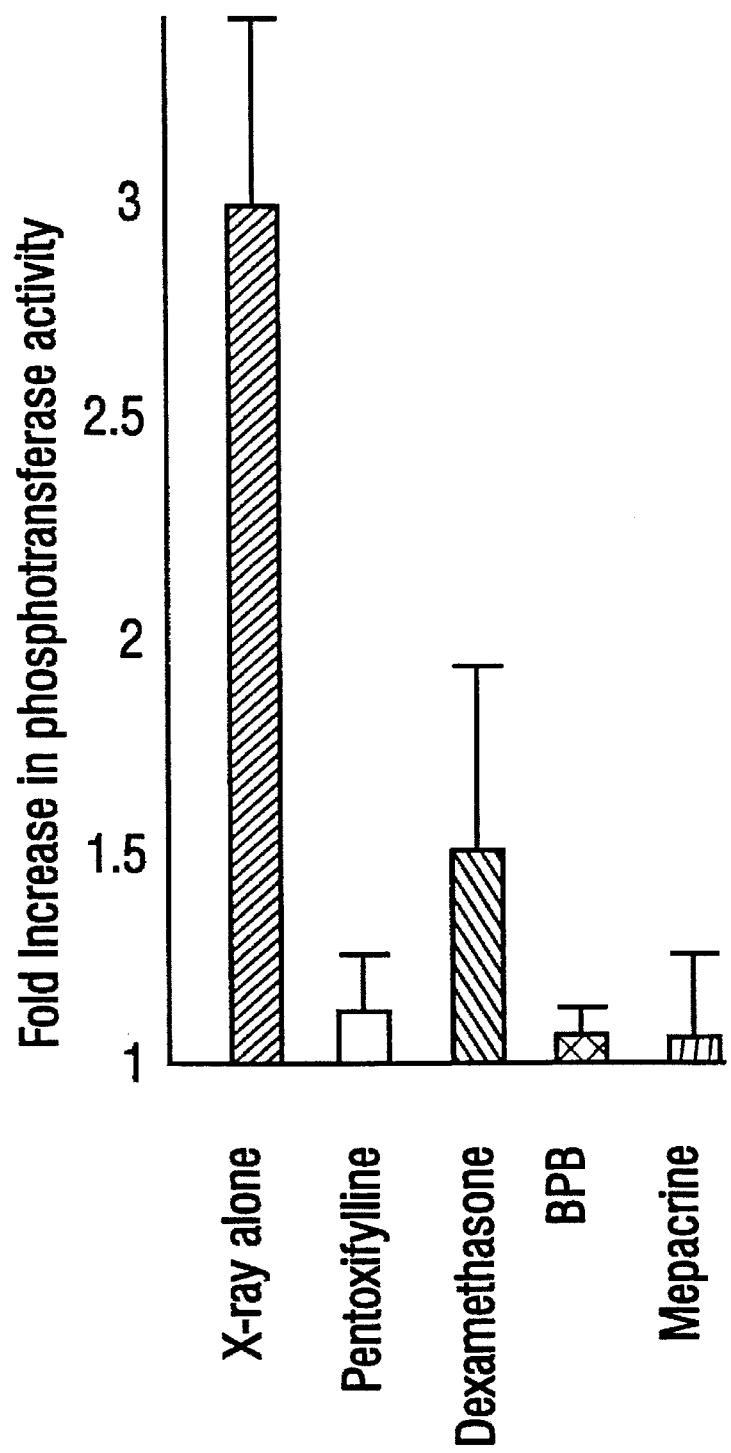
FIG. 4 X-ray-induced PKC Activation. Mepacrine 20 µM, BPB, Dexamethasone or pentoxifylline were added to EL-60 cell cultures 1 hr prior to γ-irradiated with 10.8 Gy using a Cobalt-60 source (Gammacell 220) at a dose rate of 2.7 Gy/second. Cells were placed on ice and lysis buffer was added at 60 seconds following irradiation. Phosphotransferase activity was assayed using $^{32}$P-ATP/substrate containing 5×10$^7$ CPM/ml of $^{32}$P-ATP (New England Nuclear) and synthetic peptide Gln-Lys-Arg-Pro-Ser(8)-Gln-Arg-Ser-Lys-Tyr-Leu. Phosphorylation rates were normalized to 10$^6$ cells per assay. Studies were performed 3 times and results are presented as the mean ± standard error.

The effects of the phospholipase A2 inhibitors on radiation-induced protein kinase C activation PKC phosphotransferase activity is increased following the addition of arachidonate (Peters-Golden et al., 1991, McPhail et al., 1984). Taken together with the findings that PKC is activated rapidly and transiently following ionizing radiation exposure and that PKC activity is required for radiation-induced TNF gene induction in HL-60 cells (Hallahan et al., 1991b), these data suggested that arachidonate activation of PKC might be the signalling pathway which confers TNF induction. To determine whether radiation-induced arachidonate production is associated with PKC activation, the phosphotransferase activity of PKC was quantified in irradiated HL-60 cells pretreated with mepacrine, BPB, pentoxifylline or dexamethasone. Protein was extracted at 60 seconds following irradiation, and phosphotransferase activity was quantified in vitro. The PKC specific peptide substrate from myelin basic protein (Yasuda et al., 1990) and the PKC inhibitor peptide from the PKC regulatory domain (House et al., 1987) were employed to quantify PKC activity following irradiation. A 3-fold increase in phosphotransferase activity was found at 45 seconds following irradiation as compared to untreated control cells. Mepacrine, BPB, pentoxifylline and dexamethasone, added 1 hr prior to irradiation, reduced the X-ray induced increase in PKC phosphotransferase activity (FIG. 4).

Figure 5:
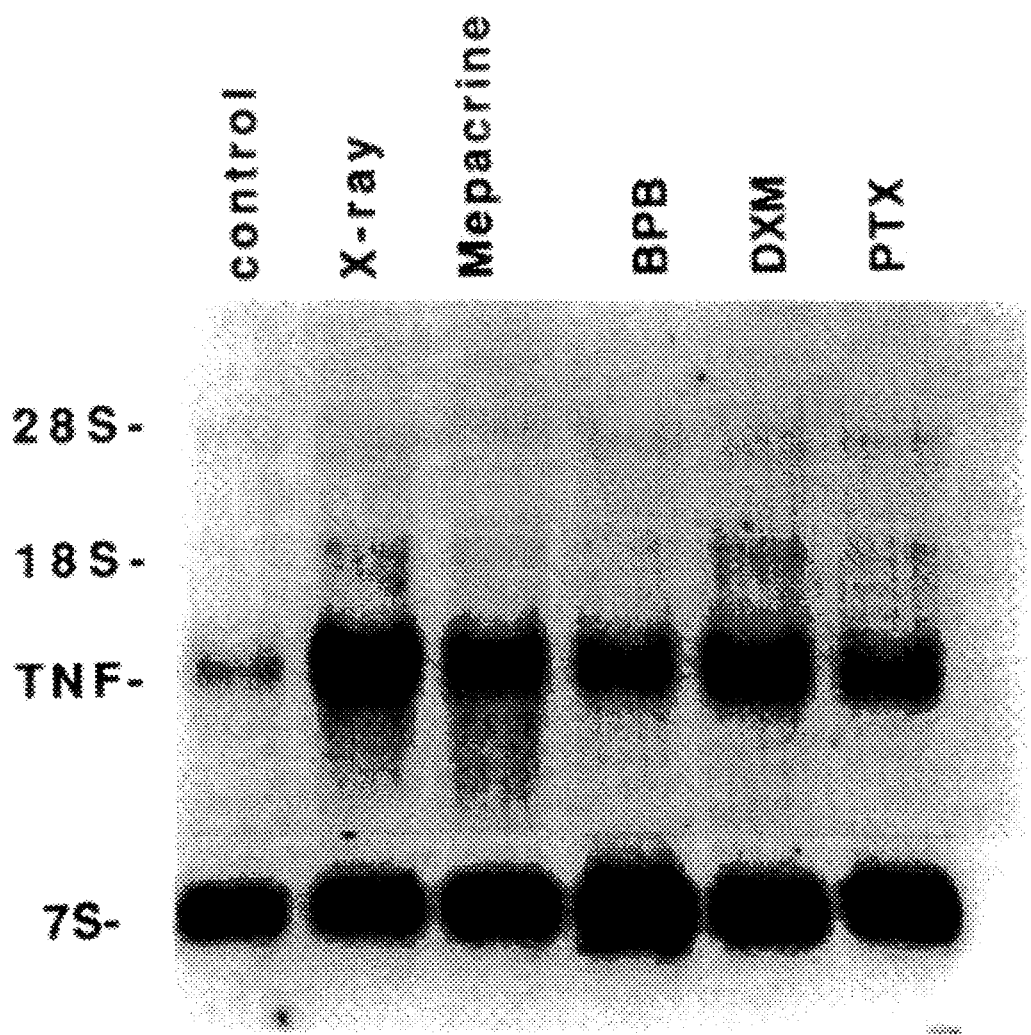
FIG. 5 X-ray-induced TNF gene expression. Mepacrine 20 µM, Dexamethasone, BPB, or pentoxifylline were added to HL-60 cell cultures 1 hr prior to irradiation with 10 Gy (1 Gy/min) using a GE Maxitron generator. RNA was extracted at 1 hour after irradiation as previously described (30). Control RNA from nonirradiated cells treated under otherwise identical conditions and RNA from irradiated cells was size fractionated by 1% agarose formaldehyde electrophoresis and hybridized to a $^{32}$P labeled TNF cDNA probe (24). 7S RNA hybridization was used to demonstrate equal loading of lanes.

The effects of the phospholipase A2 inhibitors on radiation-induced TNF gene expression Although transcription of certain radiation-inducible genes occurs through both PKC-dependent and independent signalling pathways (Datta et al., 1992), TNF induction is dependent upon PKC activation (Hallahan et al., 1991b) and thus represents a radiation-mediated gene which can be studied to determine the significance of phospholipase inhibition on radiation-mediated gene induction. Mepacrine, bromphenylbromide, pentoxifylline or dexamethasone were added to HL-60 cells 1 hr prior to x-irradiation. RNA was isolated 1 hr following irradiation at the time of peak TNF expression (Sherman et al., 1991). The finding that each of these agents each blocked radiation-induced TNF gene expression (FIG. 5) indicated that radiation-induced TNF expression is dependent on signaling through phospholipase A2. Moreover, attenuation of radiation-mediated gene induction by these phospholipase A2 inhibitors suggests that signal transduction activated by ionizing radiation is in part initiated through hydrolysis of oxidized membrane lipids.

DISCUSSION

Second messengers such as diacylglycerol (DAG), arachidonic acid and calcium participate in PKC activation in response to a number of external stimuli (Nishizuka, 1992). The inventors have investigated the mechanism of PKC activation following irradiation by analyzing the second messengers diacylglycerol, arachidonic acid and calcium which participate in PKC activation in response to a number of external stimuli (Nishizuka 1992). It was found that diacylglycerol levels were not increased following irradiation as determined by the DAG kinase assay. Furthermore, intracellular calcium flux did not occur as determined by quantifying UV absorption in fura-2 treated cells during irradiation with $^{90}$Sr (60 cGy/sec) (Hallahan et al., 1994 (in press)). Taken together, these data support the finding that phosphoinositol-specific phospholipase C is not activated during irradiation since the coincident increase in inositol triphosphate would mobilize intracellular $Ca^{++}$.

The acute effects of ionizing radiation on the lung has been shown to be associated with endothelial leakage (Ward et al., 1993a). Corticosteroids prevent the acute effect when given to animals at the time of irradiation, but this treatment did not affect lung fibrosis (Ward et al., 1993b) indicating that steroids prevent the inflammatory component of radiation injury but not the fibrotic component. In the present study, arachidonic acid release was reduced when irradiated cells were pretreated with pentoxifylline, dexamethasone or BPB. These findings are significant in that the reduction in radiation-mediated phospholipase A2 activity in turn diminished PKC activation and TNF induction.

Lipid oxidation occurs in the cell membrane of irradiated cells (Yatvin et al., 1979). Indeed, the probable mechanism of arachidonic acid release following irradiation is phospholipase $A_2$-mediated hydrolysis of oxidized membrane lipids. In support of this hypothesis, whole body irradiation of animal models results in increased arachidonic acid metabolites (Eldor et al., 1979). Oxidative injury following $H_2O_2$ treatment results in phospholipase $A_2$-mediated arachidonic acid release in epithelial and endothelial cells (Gustafson et al., 1991, Au et al., 1987, Sevanian et al., 1983).

Phosphatidylcholine hydrolysis to arachidonic acid is reduced by pentoxifylline in platelets stimulated with thrombin (Rossignol et al., 1988). In concert with these findings and the demonstration that arachidonic acid activates PKC both in vitro and in vivo (Sporn et al., 1990, Khan et al., 1991, Fan et al., 1990, Lester et al., 1991) the inventors have found that inhibition of phospholipase A2 attenuates radiation-induced PKC activation. These results demonstrate that fatty acid hydrolysis an early step in a signalling pathway activated by ionizing radiation which may be independent of DNA damage. On the basis of these results, it is surmised that evolution of phospholipase A2-dependent signaling pathways provides a mechanism for higher eukaryotes to respond to reactive oxygen intermediates with cytokine production. In support of this consideration, Neta et al have shown that TNF protects hematopoietic cells from killing by ionizing radiation (Neta et al., 1991).

A practical application of these findings relates to reduction of radiation sequelae during the treatment of cancer.

Although the effects of ionizing radiation on proliferating cell renewal systems are theorized to be due to the direct killing effects of radiation on stem cells within the injured organ, other work has suggested that TNF induction plays a role in the acute effects of radiation therapy (reviewed in Weichselbaum et al., 1993). For example, elevated TNF serum levels in patients receiving total body irradiation prior to bone marrow transplantation is associated with a greater incidence of complications such as mucositis, pneumonitis, hepatitis and nephritis than in patients with relatively lower TNF serum levels (Holler et al., 1992). Because TNF induction is associated with acute and subacute complications of therapeutic radiation, inhibition of phospholipase A2 represents a means of abating these sequelae. Indeed, pharmacologic agents used to ameliorate the acute and subacute sequelae of radiotherapy include glucocorticoids and pentoxifylline (Phillips et al., 1975, Gross, 1980, Bianco et al., 1991). For example, acute effects of radiation, such as pneumonitis and the central nervous system syndrome, have been abated by these drugs (Phillips et al., 1975).

The identification of a signal transduction pathway responsible for radiation-mediated arachidonic acid production, PKC activation and TNF induction may allow for rational design of radioprotective drugs that do not adversely affect tumor cure rates and avoid the serious side effects of glucocorticoids. Such strategies of radioprotection offer new avenues to enhance the therapeutic ratio in clinical oncology.

EXAMPLE III

Assessment of the Effects of Radiation Exposure on Cells in the Absence of or Reduction in TNF Levels.

Since TNF induction results from radiation exposure in certain cells, methods have been devised to assess cell function and cytotoxicity following exposure to radiation alone, or in combination with particular proteins or antisense molecules that have an activity on cell function. These studies are performed in the absence or reduction in the amounts of TNF in these particular cells. Reduction of TNF is accomplished by treating cells with lipoxygenase inhibitors prior to irradiation and measuring cell survival, growth rates, protein and mRNA levels. Additionally, radiation inducible promoters unaffected by the lipoxygenase inhibitors, such as Egr-1 and c-jun, are used to express various proteins or antisense molecules, such as those that are involved in cytotoxicity.

This method allows easy assessment of cell function following irradiation without the interfering effects of TNF activity.

METHOD

HL-60 cells are maintained in RPMI medium and 20% fetal bovine serum (FBS), 100 units/ml penicillin and 100 µg/ml streptomycin. During survival analysis, the colony forming assay was used and cells are cultured in semisolid medium consisting of 0.8% methylcellulose in RPMI and 20% fetal calf serum.

Genes encoding the messenger RNA for proteins to be expressed in cells following irradiation include, for example, radioprotective agents such as interleukin-1 or interleukin-6. These genes are operatively linked to a radiation inducible promoter that is unaffected by lipoxygenase inhibitors, for example Egr-1 or c-jun.

For transfection, the HL-60 cells are resuspended at a concentration of $2 \times 10^7$ cells/ml in cold RPMI media buffered with HEPES, and 0.5 ml is aliquoted into each electroporation cuvette. Linearized DNA is then added to the cells in the cuvette. The solution is gently mixed and allowed to incubate at room temperature for 5 minutes. The cells are transfected by electroporation at 350 V/960 µF. The cuvettes are then allowed to stand for 15 minutes after which the cells are cultured in complete medium for 48 hours. The cells are subcloned in G418 (1200 µg/ml) by plating 0.5 cells/well in 96 well plates. These subclones are grown and maintained in G418 and tested for induction of, for example, the radiosensitizing gene or other gene to be studied.

At least one hour prior to irradiation, 1 µM ketoconazole is added to the cell cultures. Alternatively, other lipoxygenase inhibitors such as zileuton may be added at similar concentrations. The cells are then irradiated with 20 Gy ionizing radiation, because this dose produces maximal induction of transcription following irradiation and that this is a standard radiation dosage used in animal tumor studies (Bauman, et al. 1991, Budach et al. 1993).

RNA analysis following irradiation

RNA is extracted at 1 hr following irradiation using the single step guanidinium thiocyanate-phenol/chloroform method (Chomczynski et al., 1987). Control RNA from nonirradiated cells treated with otherwise identical conditions and RNA from irradiated cells is size fractionated by 1% agarose formaldehyde electrophoresis. Ethidium bromide staining of the RNA demonstrates equal loading of each lane. RNA gels are then transferred to a nylon membrane. Northern blots are hybridized to $^{32}p$ labeled probes for the gene of interest, Egr-1 and c-jun cDNA probes (Cao et al., 1990, Hatori et al., 1988, Spriggs et al., 1990), followed by autoradiography for 3 days at $-85°$ C. with intensifying screens.

EXAMPLE IV

Protocol for Treatment of Cancer with X-ray Induced Genes and the Modulation of Radiation Induced Sequelae by Lipoxygenase Inhibitors For treatment of patients with cancer, the following steps are followed:
1. Prepare a DNA molecule (genetic construct or vector) comprising a radiation inducible promoter operatively linked to an encoding region that encodes a polypeptide or any other useful component, such as an antisense molecule with a sequence that is the antisense version to an oncogene. This is exemplified by a construct that comprises a CArG domain of an Egr-1 promoter and the gene for a polypeptide.
2. The construct is then administered to the patient to be treated. This administration may be in the form of intravenous infusion of naked DNA, or through the use of viral delivery vectors. Exemplary viral vectors are retrovirus that is self-inactivating, adenovirus, or adeno-associated virus. If a retrovirus is employed, lymphokine-activated killer (LAK) cells are first infected with the retrovirus containing the construct, then administered to the patient.
3. At least one hour prior to irradiation, the patient is given a dose of a lipoxygenase inhibitor, preferably ketoconazole. Doses may range from 100 mg to 2 g per day. Alternatively, zileuton is administered at 800 mg 1 hour prior to irradiation.
4. The region is irradiated.

EXAMPLE V

Phase I Protocol for Treatment with Ketoconazole and Radiation

To reduce acute and subacute radiation sequelae, patients with incurable, locally advanced or metastatic cancer are treated and evaluated for performance status and laboratory parameters including CR>1.5 mg/dl; Bilirubin>1.5 mg/dl; SGOT>3×upper limit of normal; PT>1.3×upper limit of control; PTT>1.3×upper limit of control; WBC<3500/mm$^3$ Granulocyte count<1500/mm$^3$; Platelet count<100,000/mm$^3$; Hgb<10 gm/dl Ketoconazole (200 mg) is given orally prior to irradiation. After one hour, the patient is administered a dose of radiation of approximately 200–300 cGy. The procedure is repeated in daily intervals until a total dose of 3000 to 7000 cGy is reached.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Au, A., Chan, P., & Fishman, R. (1985)*J. Cell. Biochem.* 27, 449–53.
Baumann, M., DuBois, W., Pu, A., Freeman, J., Suit, H. (1992) *Int. J. Radiat. Oncol. Biol. Phys.* 23, pp. 803–809.
Bell, R. M., Hannun, Y. & Loomis, C. (1986) *Meth Enzym* 124, 353–7.
Bianco, J., Applebaum, F., Nemunaitis, J., Almgren, J., Andrews, F., Kettner, P., Shields, A. and Singer, J. W. (1991) *Blood* 78, 1205–11.
Budach, W., Budach, V., Stuschke, M., Dinges, S., Sack, H. (1993) *Int. J. Radiat. Oncol. Biol. Phys.* 25, pp. 259–268.
Chomczynski, P. & Sacchi, N. (1987)*Analytical Biochemistry* 162, 156–9.
Cole, G., Schild, D., Lovett, S. & Mortimer, R. (1987)*Molec Cell Biol* 7, 1078–84.
Datta, R., Hallahan, D., Kharbanda, S., Rubin, E., Sherman, M., Huberman, E., Weichselbaum, R. & Kufe, D. (1992) *Biochemistry* 31, 8300–6.
Eldor, A., Vlodavsky, I., Fuks, Z., Matzner, Y. & Rubin, D. B. (1989) *Prostaglandins leukotrienes and essential fatty acids* 36, 251–8.
Enoch, T., Carr, A. & Nurse, P. (1992) *Genes Devel.* 6, 2035–46.
Fan, X. T., Huang, X. P., Da, S. C. & Castagna, M. (1990) *Biochem Biophys Res Commun* 169, 933–40.
Godfrey, R., Johnson, W. & Hoffstein, S. (1987) *Biochem Biophys Res Commun* 142, 235–41.
Godson, C., Weiss, B. A. & Insel, P.A. (1990) *J Biol Chem* 265, 8369–72.
Gross, N.J. (1980) *J Clin Invest* 66, 504–10.
Gustafson, C., Lindahl, M. & Tagesson, C. (1991) *Scand. J. Gastroenterol* 26, 237–47.
Hallahan, D., Virudchalam, S., Schwartz, J., Panje, N., Mustafi, R. & Weichselbaum, R. (1992) *Radiat. Res.* 129, 345–50.
Hallahan, D. E., Sukhatme, V. P., Sherman, M. L., Virudachalam, S., Kufe, D. W. & Weichselbaum, R. R. (1991) *Proc. Natl. Acad. Sci.* 88, 2152–60.
Hallahan, D., Virudachalam, S., Sherman, M., Kufe, D. & Weichselbaum, R. (1991) *Cancer Research* 51, 4565–9.
Hallahan, D. E., Spriggs, D. R., Beckett, M. A., Kufe, D. W. & Weichselbaum, R. R. (1989) *Proc. Natl. Acad. Sci. U S A* 86, 10104–7.
Hallahan, D. E., Bleakman, D., Virudachalam, S., Lee, D., Grdina, D., Kufe, D. & Weichselbaum, R. (1994) *Rad Res. In Press.*
Han, J., Thompson, P. & Beutler, B. (1990) *J. Exp. Med.* 172, 391–6.
Herrlich, P., Ponta, H. & Rahmsdorf, H. (1992) *Rev. Physiol. Biochem. Pharmacol.* 119, 187–223.
Holler, E., Kolb, H., Moller, A., Kempeni, J., Liesenfeld, S., Pechumer, H., Lehmacher, W., Ruckdeschel, G., Gleixner, B., Riedner, C., Ledderose, G., Brehm, G., Mittermuller, J. and Wilmanns, W. (1990) *Blood* 75, 1011–16.
House, C. & Kemp, B. E. (1987) *Science* 238, 1726–28.
Jones, J. & Prakash, L. (1991) *Nucl. Acid Res.* 19, 893–5.
Khan, W., el, T. S. & Hannun, Y. A. (1991) *Febs Lett* 292, 98–102.
Kastan, M., Zhan, Q., El-Deiry, W., Carier, F., Jacks, T., Walsh, W., Plunkett, B., Vogelstein, B. & Fornace, A. (1992) *Cell* 71, 587–97.
Lester, D. S., Collin, C., Etcheberrigaray, R. & Alkon, D. L. (1991) *Biochem Biophys Res Commun* 179, 1522–6.
Lognonne, J. L., Ducousso, R., Rocquet, G. & Kergonou, J. F. (1985) *Biochime* 67, 1015–21 44. G. Hahn, M. Menconi, M. Cahill & P. Polgar. (1983) *Prostaglandins* 25, 783–91.
McMillan, R. M. and Walker, E. R. H., (1992) *Trends in Pharm. Sci.* 13, 323–330.
McPhail, L., Clayton, C. & Snyderman, R. (1984) *Science* 224, 622–5.
Murakami, K., Chan, S. & Routtenberg, A. (1986) *J. Biol. Chem.* 261, 15424–9.
Neta, R., Oppenheim, J. J., Schreiber, R. D., Chizzonite, R., Ledhey, G. D. & MacVittie, T. J. (1991) *J. Exp. Med.* 173, 1177–82.
Nishizuka, Y. (1992) *Science* 258, 607–14.
Peppelenbosch, M., Tretoolen, L., Hage, W. & de Laat, S. (1993) *Cell* 74, 565–15.
Peters-Golden, M., McNish, R. W., Sporn, P. H. & Balazovich, K. (1991) *Am J Physiol.* 261, L462–71.
Phillips, T., Wharam, M. & Margolis, L. (1975) *Cancer* 35, 1678–84.
Rao, G., Lassegue, B., Griendling, K., Alexander, R. & Berk, B. (1993) *Nucl. Acid. Res.* 21, 1259–63.
Rossignol, L., Plantavid, M., Chap, H. & Douste-Blazy, L. (1988) *Biochem Pharm* 37, 3229–36.
Sambrook et al. (1989). Molecular cloning: A laboratory manual. Cold Spring Harbor Laboratory. Cold Spring Harbor, N.Y. Sevanian, A., Kelly, S. & Montestrugue, S. (1983) *Arch. Biochem Biophys.* 223, 441–52.
Shasby, D., Winter, M. & Shasby, S. (1988) *Cell Physiol* 24, C781.–8.
Sherman, M. L., Datta, R., Hallahan, D., Weichselbaum, R. R. & Kufe, W. (1991) *J. Clin. Invest.* 87, 1794–7.
Sporn, P. H., Marshall, T. M. & Peters-Golden, M. (1990) *Biochim Biophys Acta* 1047, 187–91.
Spriggs, D., Sherman, M., Imamura, K., Mohri, M., Rodriguez, C., Robbins, G. & Kufe, D. (1990) *Cancer Res.* 50, 7101–7.
Strieter, R. M., Remick, D. G., Ward, P. A., Spengler, R. N., Lynch, J. P. III, Larrick, J. a Kunkel, S. L. (1988) *Biochem. Biophys. Res. Comm.* 155, 1230–6.

Uckun, F., Tuel-Ahlgren, L., Song, C., Waddick, K., Myers, D., Kirihara, J., Ledbetter, J. & Schieven, G. (1992) *Proc. Natl Acad Sci* 89, 9005–9.

van Kuijk, F. J., Handelman, G. J. & Dratz, E. A. (1987) *Trends Biochem Sci* 12, 31–4.

Walker, G. C. (1985) *Ann. Rev. Biochem.* 54, 425–57.

Ward, H., Kemsley, L., Davies, L., Holecek, M. & Berend, N. (1993) *Rad. Res.* 136, 15–21.

Ward, H., Kemsley, L., Davies, L., Holecek, M. & Berend, N (1993) *Rad. Res.* 136, 2–8.

Weichselbaum, R., Hallahan, D. & Chen, G. in *Biological and Physical Basis to Radiation Oncology*, eds. Holland & Frei (Lea and Febiger, Malvern, Pa.; 1993). Wright, T., Rangan, L., Shin, H., Raben, D. (1988) *J. Biol. Chem.* 263, 9374–80.

Yasuda, I., Kishimoto, A., Tanaka, S.-I., Masahiro, T., Sakurai, A. & Nishizuka, Y. (1990) *Biochem. and Biophys Res Comm.* 166, 1220–7.

Yates, R. A., et al., (1992) *Am. Rev. Resp. Dis.* 145, A745.

Yatvin, M., Gipp, J. & Dennis, W. (1979) *Int. J. Rad. Biol.* 25, 539–48.

Zhou, Z. & Elledge, S. (1992) *Genetics* 131, 851–66.

What is claimed is:

1. A process of inhibiting the growth of a tumor in a mammal and reducing acute radiation sequelae, comprising the steps of:

(a) delivering to the mammal a therapeutically effective dose of a lipoxygenase inhibitor;

(b) delivering to the tumor a therapeutically effective amount of a DNA molecule comprising a radiation inducible promoter unaffected by the lipoxygenase inhibitor operatively linked to an encoding region that encodes a polypeptide having the ability to inhibit growth of a tumor cell, which encoding region is operatively linked to a transcription terminating region; and (c) exposing the tumor to an effective expression-inducing dose of ionizing radiation, whereby tumor growth is inhibited.

2. A method of assessing growth inhibition in a cell under conditions of reduced or absent radiation-induced cytokine expression comprising the steps of:

(a) delivering to the cell a DNA molecule comprising a radiation inducible promoter unaffected by inhibitors of lipoxygenase operatively linked to an encoding region that encodes a polypeptide having the ability to inhibit growth of a tumor cell, which encoding region is operatively linked to a transcription terminating region;

(b) contacting the cell with an inhibitor of lipoxygenase;

(c) exposing said cell to an effective expression-inducing dose of ionizing radiation; and (d) assessing growth inhibition.

3. The method of claim 2, wherein the inhibitor of lipoxygenase is ketoconazole, fluconazole, itraconazole, AA 861, cirsiliol, zileuton, BWA4C, ICID2138, piriprost, or diethylcarbamazine.

4. The method of claim 3, wherein the inhibitor of lipoxygenase is ketoconazole.

* * * * *

UNITED STATES PATENT AND TRADEMARK OFFICE
CERTIFICATE OF CORRECTION

Page 1 of 2

PATENT NO. : 5,641,755

DATED : June 24, 1997

INVENTOR(S) : Weichselbaum et al.

It is certified that error appears in the above-identified patent and that said Letters Patent is hereby corrected as shown below:

Title page, item [57],

In the Abstract:
Line 7, please delete the second "of".

In the Specification:
Column 1, line 9, please replace "rights," with --rights--.
Column 2, line 33, please replace "hydrolysis" with --hydrolyses--.
Column 5, line 56, please replace "EL-60" with --HL-60--.
Column 6, line 51, please replace "Cyclooxygenase" with --cyclooxygenase--.
Column 8, line 56, please replace "P1.2" with --P1.2.--.
Column 9, line 37, please replace "post transcriptional" with --posttranscriptional--.
Column 10, line 18, please replace "c-jun" with --c-Jun--; and
line 29, please replace "los" with --fos--.
Column 11, line 47, please replace ">5-to 10 fold" with -->5- to 10-fold--.
Column 12, line 59, please replace "anglogenesis" with --angiogenesis--.
Column 20, line 6, please replace "µof" with --µl of--; and
line 8, please replace "micelies" with --micelles--.

UNITED STATES PATENT AND TRADEMARK OFFICE
CERTIFICATE OF CORRECTION

PATENT NO. : 5,641,755
DATED : June 24, 1997
INVENTOR(S) : Weichselbaum et al.

It is certified that error appears in the above-identified patent and that said Letters Patent is hereby corrected as shown below:

In the Specification:
Column 24, line 28, please replace "$^{32}$p" with --$^{32}$P--.
Column 26, line$^{66}$, please replace "a" with --&--.
Column 27, please replace lines 11-15 with the following:
--Weichselbaum, R., Hallahn, D. & Chen, G. in *Biological and Physical Basis to Radiation Oncology*, eds. Holland & Frei (Lea and Febiger, Malvern, Pa.; 1993).

Wright, T., Rangan, L., Shin, H., Raben, D. (1988) *J. Biol. Chem.* 263, 9374-80.--

Signed and Sealed this

Eighteenth Day of November 1997

Attest:

BRUCE LEHMAN

*Attesting Officer*   Commissioner of Patents and Trademarks